US 9,937,234 B2

(12) United States Patent
Hughes et al.

(10) Patent No.: US 9,937,234 B2
(45) Date of Patent: Apr. 10, 2018

(54) COMPOSITIONS AND METHODS FOR USING AND IDENTIFYING ANTIMICROBIAL AGENTS

(71) Applicant: UNIVERSITY OF VIRGINIA PATENT FOUNDATION, Charlottesville, IN (US)

(72) Inventors: Molly A. Hughes, Charlottesville, VA (US); Borna Mehrad, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/031,517

(22) PCT Filed: Oct. 21, 2014

(86) PCT No.: PCT/US2014/061583
§ 371 (c)(1),
(2) Date: Apr. 22, 2016

(87) PCT Pub. No.: WO2015/061322
PCT Pub. Date: Apr. 30, 2015

(65) Prior Publication Data
US 2016/0271220 A1    Sep. 22, 2016

Related U.S. Application Data

(60) Provisional application No. 61/894,484, filed on Oct. 23, 2013.

(51) Int. Cl.
*C12Q 1/18* (2006.01)
*A61K 45/06* (2006.01)
*A61K 38/19* (2006.01)

(52) U.S. Cl.
CPC ............ *A61K 38/195* (2013.01); *A61K 45/06* (2013.01); *C12Q 1/18* (2013.01)

(58) Field of Classification Search
CPC ...................................................... C12Q 1/18
See application file for complete search history.

(56) References Cited

U.S. PATENT DOCUMENTS

2004/0122212 A1    6/2004  Cosson et al.
2005/0282242 A1   12/2005  Rothstein et al.
2006/0178322 A1    8/2006  Schechter
2012/0321687 A1*  12/2012  Hughes ............... C07K 14/521
                                                 424/405

FOREIGN PATENT DOCUMENTS

WO        2011/103458        8/2011
WO    WO 2012/151474    * 11/2012

OTHER PUBLICATIONS

Muraraka et al., "Metabolic Analysis of Wild-type *Escherichia coli* and a Pyruvate Dehydrogenase Complex (PDHC)-deficient Derivative Reveals the Role of PDHC in the Fermentative Metabolism of Glucose," The Journal of Biological Chemistry, Oct. 8, 2010, vol. 285, pp. 31548-31558.
International Search Report for PCT/US14/061583, dated Feb. 5, 2015.
Cole et al., "Cutting Edge: IFN-Inducible ELR-CXC Chemokines Display Defensin-Like Antimicrobial Activity," The Journal of Immunology, The American Association of Immunologists, US, vol. 167, No. 2, Jul. 15, 2007, pp. 623-627.
Perez-Gil et al., "Mutations in *Escherichia coli aceE* and *ribB* Genes Allow Survival of Strains Defective in the First Step of the Isoprenoid Biosynthesis Pathway," PLOS One, vol. 7, No. 8, Aug. 21, 2012, p. e43775.
Ren et al., "Structure-based rational design of novel hit compounds for pyruvate dehydrogenase multienzyme complex E1 components from *Escherichia coli*," Bioorganic & Medicinal Chemistry vol. 19, No. 24, Oct. 19, 2011, pp. 7501-7506.
Yang et al., "Many chemokines including CCL20/MIP3α display antimicrobial activity," Journal of Leukocyte Biology, vol. 74, No. 3, Sep. 1, 2003, pp. 448-455.

* cited by examiner

*Primary Examiner* — Christina Bradley
(74) *Attorney, Agent, or Firm* — Barnes & Thornburg LLP

(57) ABSTRACT

As disclosed herein methods are provided to identify compounds with antimicrobial activity, and methods for treating subjects by administering the compounds. In particular, the invention provides methods for treating and/or preventing microbial diseases and infections. One aspect of the present invention is directed to the identification of bactericidal compounds that function like chemokines. In one embodiment compounds are identified that bind to the extracellular domains of *Bacillus anthracis* FtsX. Compounds that bind to FtsX are then screened for bactericidal activity. In one embodiment compounds are screened to identify compounds that bind to the peptide.

8 Claims, 9 Drawing Sheets

COMPOSITIONS AND METHODS FOR USING AND IDENTIFYING ANTIMICROBIAL AGENTS

CROSS-REFERENCE TO RELATED APPLICATIONS, AS FOLLOWS

This application is a U.S. national application under 37 C.F.R. § 371(b) of International Application Serial No. PCT/US2014/061583 filed Oct. 21, 2014 which claims priority under 35 USC § 119(e) to U.S. Provisional Application Ser. No. 61/894,484, filed Oct. 23, 2013, the disclosures of which are incorporated herein by reference.

GOVERNMENT RIGHTS

This invention was made with Government support under Grant No. AI099097, awarded by the National Institutes of Health. The Government has certain rights in the invention.

BACKGROUND

Since 1996, there has been a dramatic and alarming increase in the isolation of multi-drug resistant (MDR) Gram-negative organisms, such as *Klebsiella pneumoniae* and *Escherichia coli*, from patients with bloodstream infections, pneumonias, and intra-abdominal infections. Multi-drug resistance among Gram-negative organisms typically denotes bacteria resistant to three or more classes of antibiotics. The increase in MDR Gram-negative bacteria has now been recognized throughout the world and in a number of states within the United States. These MDR bacteria are resistant to not only the cephalosporins but also to the carbapenems (imipenem, meropenem, ertapenem, and doripenem), which have traditionally been the last line of antimicrobial defense against the cephalosporin-resistant organisms. Given that the carbapenems are not effective against these carbapenem-resistant Enterobacteriaceae (CRE), there are now very few antimicrobial options available. In the absence of any new antibiotics to combat these pathogens, healthcare workers are being forced to use older antibiotics such as colistin, which was used in the 1970's and has significant and serious side effects. Moreover, colistin-resistant bacteria are now being identified, reducing the available armamentarium of antimicrobials to one or zero antibiotics. Thus, new therapeutic strategies are urgently needed to fight these MDR Gram-negative pathogens, which carry a high morbidity and mortality rate.

Much of the focus in the last 15 years has been on resistance in Gram-positive organisms (e.g., methicillin-resistant *Staphylococcus aureus* (MRSA) and vancomycin-resistant *enterococcus* (VRE)), although Gram-negative bacteria account for a large proportion of nosocomial infections. For example, in New York City, Gram-negative organisms account for at least 8% of nosocomial infections, and at least half of those are MDR, carbapenem-resistant bacteria.

The list of antibiotics available to treat infections with any of these MDR CRE organisms is limited from very few to none. Novel approaches are critically needed for identifying new therapies for treating such pathogens, especially since simply producing newer generation antibiotics of the same class is unlikely to provide much benefit since cross-resistance can rapidly develop.

There is a long felt need in the art for compositions and methods useful for fighting Gram-negative organisms and infections caused by these organisms. The present invention satisfies these needs.

Chemokines are chemotactic cytokines that are important regulators of leukocyte-mediated inflammation and immunity in response to a variety of diseases and infectious processes in the host. Chemokines are a superfamily of homologous 8-10 kDa heparin-binding proteins, originally identified for their role in mediating leukocyte recruitment.

The four major families of chemokine ligands are classified on the basis of a conserved amino acid sequence at their amino terminus, and are designated CXC, CC, C, and CX3C sub-families (where "X" is a nonconserved amino acid residue).

The interferon-inducible (ELR-) CXC chemokines are one of the largest families of chemokines, and each member of this group contains four cysteine residues. Most chemokines are small proteins (8-10 kDa in size), have a net positive charge at neutral pH, and share considerable amino acid sequence homology. Structurally, the defining feature of the CXC chemokine family is a motif of four conserved cysteine residues, the first two of which are separated by a non-conserved amino acid, thus constituting the Cys-X-Cys or 'CXC' motif. This family is further subdivided on the basis of the presence or absence of another three amino acid sequence, glutamic acid-leucine-arginine (the 'ELR' motif), immediately proximal to the CXC sequence. The ELR-positive (ELR+) CXC chemokines, which include IL-8/CXCL8, are potent neutrophil chemoattractants and promote angiogenesis. Among the ELR-negative (ELR-) CXC chemokines, CXCL9, CXCL10 and CXCL11, are potently induced by both type 1 and type 2 interferons (IFN-α/β and IFN-γ, respectively). These Interferon-inducible (ELR-) CXC chemokines are generated by a variety of cell types (including monocytes, macrophages, lymphocytes, and epithelial cells), and are extremely potent chemoattractants for recruiting mononuclear leukocytes, including activated Th1 CD4 T cells, natural killer (NK) cells, NKT cells, and dendritic cells to sites of inflammation and inhibiting angiogenesis.

The chemokine receptors are a family of related receptors that are expressed on the surface of all leukocytes. The shared receptor for CXCL9, CXCL10, and CXCL11 is CXCR3. Through their interaction with CXCR3, the ligands CXCL9, CXCL10 and CXCL11 are the major recruiters of specific leukocytes, including CD4 T cells, NK cells, and myeloid dendritic cells. Importantly, this chemokine ligand-receptor system is at the core of a positive feedback loop escalating Th1 immunity, whereby cytokines such as interleukin (IL)-12 and IL-18 (released by myeloid accessory cells) activate local NK cells to produce IFN-γ, which then induces generation of CXCL9, CXCL10, and CXCL11, which then recruits CXCR3-expressing cells that act as a further source of IFN-γ, which then induces further production of CXCL9, CXCL10, and CXCL11. Consistent with the importance of these interferon-inducible (ELR-) CXC chemokines in promoting Th1-mediated immunity, CXCR3 and its ligands have been documented to play a critical role in host defense against many micro-organisms, including viruses, *Mycobacterium tuberculosis*, other bacteria, and protozoa.

Independent of their role in CXCR3-dependent leukocyte recruitment, CXCL9, CXCL10, and CXCL11 have recently been found to display direct antimicrobial properties that resemble those of defensins. These antimicrobial effects were first demonstrated in 2001 against *Escherichia coli* and *Listeria monocytogenes*. Subsequently, an increasing number of chemokines have been shown to have antimicrobial activity against various strains of bacteria and fungi, including *E. coli, S. aureus, Candida albicans*, and *Cryptococcus neoformans*.

There is a long felt need in the art for new compositions and methods useful as antimicrobial agents, as well as targets for antimicrobial agents. The present invention satisfies these needs.

SUMMARY OF THE INVENTION

One aspect of the present invention is directed to the identification of bactericidal compounds that function like chemokines. In one embodiment compounds are identified that bind to the extracellular domains of *Bacillus anthracis* FtsX (SEQ ID NO: 10). Compounds that bind to FtsX are then screened for bactericidal activity. In one embodiment compounds are screened to identify compounds that bind to the peptide KVEQDVEIRVHIDPAAKEADQKKLEDD (SEQ ID NO: 18).

In accordance with one embodiment a method is provided for identifying anti-bacterial agents that operate through a similar mechanism of action as chemokines, more particularly of CXC10. In one embodiment the method comprises contacting a standard bacterial strain, and a derivative of that standard bacterial strain, with a candidate compound. The derivative strain is one that has been modified to differ from standard strain by a mutation that makes the strain pyruvate dehydrogenase complex (PDHC)-deficient. After contact with the candidate compound, both bacterial strains are cultured under conditions favorable for growth and compounds are identified that inhibit the growth of the standard bacterial strain to a greater extent than the derivative strain. In one embodiment compounds are selected that inhibit the standard strain by more than 2×, 3×, 5×, 10× or 50× relative to the inhibition of the corresponding derivative strain that is pyruvate dehydrogenase complex (PDHC)-deficient. In accordance with one embodiment the bacterial strains used in the method are *E. coli* or *B. anthracis* strains. In one embodiment the PDHC-deficient bacterial strain is a pyruvate dehydrogenase complex subunit deletion mutant selected from the group consisting of ΔaceE, ΔaceF, and ΔlpdA. In one embodiment the bacterial strain is *E. coli* and the pyruvate dehydrogenase complex subunit deletion mutant is ΔaceE. In one embodiment the method of screening for anti-bacterial agents that operate through a similar mechanism of action as chemokines further comprises a step of identifying compounds that bind to FtsX, and more particularly to the *B. anthracis* FtsE/X complex. In one embodiment the candidate compounds are screened to identify compounds that bind to the peptide KVEQDVEIRVHIDPAAKEADQKKLEDD (SEQ ID NO: 18).

The present disclosure provides methods for treating and/or preventing microbial diseases. The invention also provides methods for treating and/or preventing microbial infections. In accordance with one embodiment compounds that have been identified as binding to FtsX and having bactericidal activity are used for treating and/or preventing microbial infections. In accordance with one embodiment compositions comprising interferon-inducible (ELR-) CXC chemokines, including for example chemokines CXCL9, CXCL10 and CXCL11, or compounds exhibiting the same mechanism of action as chemokines CXCL9, CXCL10 and CXCL11 can be used to neutralize actively growing, as well as stationary phase, pathogenic bacteria. Furthermore, the antimicrobial compositions disclosed herein have been discovered to be surprisingly effective in neutralizing the spores of pathogenic bacteria, including spores of *Bacillus anthracis*. The compositions disclosed herein can be used as a therapeutic intervention and innovative approach for treating pulmonary and gastrointestinal bacterial pathogens, especially at a time when it is becoming increasingly clear that expanding antibiotic resistance in bacterial pathogens is moving the medical field into a post-antibiotic era.

It is disclosed herein that bacterial pyruvate dehydrogenase E1, one component of the three-part bacterial pyruvate dehydrogenase complex, is a target of CXC chemokines. In one aspect, the chemokine is CXCL10. Therefore, the present invention provides compositions and methods useful for inhibiting gram-negative bacteria, treating infections of gram-negative bacteria in subjects in need thereof, and methods for identifying agents useful for treating gram-negative bacteria infections.

The present invention provides, in one aspect, the use of CXCL10, and biologically active fragments and homologs thereof as anti-bacterial agents. In one aspect, similar chemokines are encompassed by the methods of the invention. In one aspect, a compound of the invention inhibits bacterial growth. In one aspect, a compound of the invention inhibits bacterial survival.

The present disclosure encompasses the use of any agent that targets bacterial pyruvate dehydrogenase E1 as a useful anti-bacterial agent. In one aspect, the bacteria are gram-negative bacteria. The present application discloses that bacterial pyruvate dehydrogenase E1 is a target of CXC chemokines. Therefore, the present disclosure further provides compositions, methods, and assays useful for identifying agents that target bacterial pyruvate dehydrogenase E1 and that are in turn useful as anti-bacterial agents. In one aspect, the present disclosure provides for the use of agents to inhibit bacteria or kill bacteria.

It is also disclosed herein that FtsX is the putative bacterial target for interferon-inducible (ELR-) CXC chemokines in *B. anthracis*. The present invention therefore encompasses identifying and using compounds that interact with FtsX either directly or indirectly for use as an antimicrobial agent. The present invention further provides compositions and methods useful for identifying regulators of FtsX, and therefore, identifying antimicrobial agents. In one aspect, the present invention provides compositions, methods, and assays utilizing FtsX to identify compounds that regulate FtsX function or levels or downstream activity. In one aspect, the regulation is inhibition. In one aspect, compounds identified in these assays exhibit anti-microbial activity as described herein. The types of compounds useful in the invention include, but are not limited to, proteins and peptides, as well as active fragments and homologs thereof, drugs, and peptide mimetics. In one aspect, the active fragments, homologs, and mimetics are fragments, homologs, and mimetics of the chemokines described herein.

Further embodiments of the invention include therapeutic kits that comprise, in suitable container means, a pharmaceutical formulation of at least one antimicrobial peptide of the invention. Some embodiments provide kits comprising a pharmaceutical formulation comprising at least one peptide of the invention and a pharmaceutical formulation of at least one antimicrobial agent or antibiotic. The antimicrobial peptide and antimicrobial agent or antibiotic may be contained within a single container means, or a plurality of distinct containers may be employed.

Various aspects and embodiments of the invention are described in further detail below.

BRIEF DESCRIPTION OF THE DRAWINGS

(FIG. 7A) The optical density at 600 nm (OD600) was determined for cultures of *E. coli* parent strain and ΔaceE at set time points. The ΔaceE strain initially grew more slowly, but reached similar optical densities as the parent strain at later time points. (FIG. 7B) Empty plasmid vector (pBR322) was individually transformed into electro-competent *E. coli* ΔaceE and parent strain bacteria; at set time points, OD600 was measured for cultures of each transformed strain. Growth curves for strains transformed with pBR322 were unchanged from their respective non-transformed originators (panel A). (FIG. 7C) Plasmid vector containing native aceE gene along with its promoter and ribosomal binding site (pUVA411) was individually transformed into electro-competent *E. coli* parent strain or ΔaceE. At set time points, OD600 was measured for cultures of each transformed strain. There was no difference in the growth curves of parent strain bacteria and parent strain bacteria complemented with aceE; complementation of ΔaceE bacteria with aceE, restored growth curve phenotype to that of the parent strain.

(FIG. 8A) *E. coli* parent strain remained similarly susceptible to increasing concentrations of CXCL10 when complemented with either empty vector FIG. 8B, or plasmid vector containing the aceE gene (FIG. 8C). *E. coli* parent strain bacteria, parent strain bacteria plus pBR322 (empty plasmid vector), and parent strain bacteria plus pUVA411 (aceE containing plasmid vector) were treated with increasing concentrations of CXCL10 for 2 h, after which samples were plated on LB agar and incubated overnight to determine cfu/mL. Data are expressed as log 10 cfu/mL; bars represent mean values±SEM; n=3-6 independent experiments per group. *E. coli* ΔaceE is resistant (see FIG. 8D) and remains resistant to the antimicrobial effects of CXCL10 when complemented with empty vector (FIG. 8E), however, complementation with aceE containing vector restores the parent strain susceptibility phenotype (FIG. 8F); *E. coli* ΔaceE, ΔaceE plus pBR322, and ΔaceE plus pUVA411 were treated with increasing concentrations of CXCL10 for 2 h, after which samples were plated on LB agar and incubated overnight to determine cfu/mL. Data are expressed and analyzed as detailed above.

DETAILED DESCRIPTION

Figure 1:
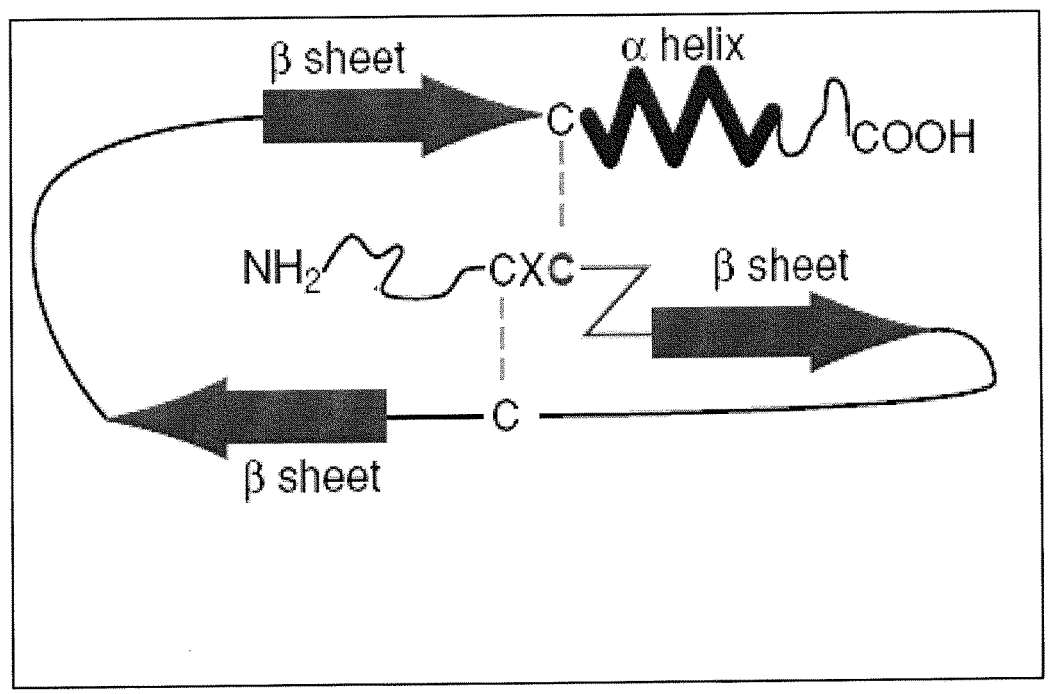
FIG. 1 is a schematic drawing of the three dimensional structure of an interferon-inducible (ELR-) CXC chemokine (figure taken from Glomski et al. (2008) Microbes Infect. 10:1398-1404).

Abbreviations and Acronyms diplicolinic acid (DPA)
monokine-induced by interferon-γ (CXCL9)
interferon-γ inducible protein of 10 kd (CXCL10)
interferon-inducible T-cell-activated chemokine (CXCL11)
monocyte chemotactic protein-1 (CCL2); RANTES (CCL5)
half maximal effective concentration (EC50)
transmission electron microscopy (TEM)
In Vivo Imaging System (IVIS)
brain-heart infusion (BHI)
phosphate buffer (PB)
charge coupled device (CCD)
colony forming unit (CFU)
interferon (IFN)
membrane-spanning domain (MSD)
nucleotide binding protein (NBP)

substrate binding protein (SBP)
toll-like receptor (TLR)
glutamic acid-leucine-arginine motif (ELR motif)

Definitions

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about" as used herein means greater or lesser than the value or range of values stated by 10 percent, but is not intended to designate any value or range of values to only this broader definition.

A disease or disorder is "alleviated" if the severity of a symptom of the disease, condition, or disorder, or the frequency with which such a symptom is experienced by a subject, or both, are reduced.

As used herein, the term "subject" refers to an individual (e.g., human, animal, or other organism) to be treated by the methods or compositions of the present invention. Subjects include, but are not limited to, mammals (e.g., murines, simians, equines, bovines, porcines, canines, felines, and the like), and includes humans. In the context of the invention, the term "subject" generally refers to an individual who will receive or who has received treatment for a condition characterized by the presence of bacteria (e.g., *Bacillus anthracis* (e.g., in any stage of its growth cycle), or in anticipation of possible exposure to bacteria. As used herein, the terms "subject" and "patient" are used interchangeably, unless otherwise noted.

As used herein, the terms "neutralize" and "neutralization" when used in reference to bacterial cells or spores (e.g. *B. anthracis* cells and spores) refers to a reduction in the ability of the spores to germinate and/or cells to proliferate.

As used herein the term "bacterial spore" or "spore" is used to refer to any dormant, non-reproductive structure produced by some bacteria (e.g., *Bacillus* and *Clostridium*) in response to adverse environmental conditions.

As used herein, the term "treating a surface" refers to the act of exposing a surface to one or more compositions of the present invention. Methods of treating a surface include, but are not limited to, spraying, misting, submerging, wiping, and coating. Surfaces include organic surfaces (e.g., food products, surfaces of animals, skin, etc.) and inorganic surfaces (e.g., medical devices, countertops, instruments, articles of commerce, clothing, etc.).

As used herein, the term "therapeutically effective amount" refers to the amount that provides a therapeutic effect, e.g., an amount of a composition that is effective to treat or prevent pathological conditions, including signs and/or symptoms of disease, associated with a pathogenic organism infection (e.g., germination, growth, toxin production, etc.) in a subject.

The terms "bacteria" and "bacterium" refer to all prokaryotic organisms, including those within all of the phyla in the Kingdom Procaryotae. As used herein, the term "microorganism" refers to any species or type of microorganism, including but not limited to, bacteria, archaea, fungi, protozoans, *mycoplasma*, and parasitic organisms.

As used herein the term "colonization" refers to the presence of bacteria in a subject that are either not found in healthy subjects, or the presence of an abnormal quantity and/or location of bacteria in a subject relative to a healthy patient.

The term "stationary growth phase" as used herein defines the growth characteristics of a given population of microorganisms. During a stationary growth phase the population of bacteria remains stable with the rate of bacterial division being approximately equal to the rate of bacterial death. This may be due to increased generation time of the bacteria. Accordingly "stationary phase bacteria" are bacteria that are in a stationary growth phase. "Exponential phase bacteria" are bacteria that are rapidly proliferating and the population is rapidly expanding, typically the number of bacteria increases at an exponential rate.

As used herein a "multi-drug resistant" microorganism or bacteria is an organism that has an enhanced ability, relative to non-resistant strains, to resist distinct drugs or chemicals (of a wide variety of structure and function) targeted at eradicating the organism. Typically the term refers to resistance to at least 3 classes of antibiotics.

Chemokines are small proteins secreted by cells that have the ability to induce directed chemotaxis in responsive cells. As used herein the term "interferon-inducible (ELR−) CXC chemokine" refers to a chemokine protein, or corresponding peptidomimetic, having a motif of four conserved cysteine residues, the first two of which are separated by a non-conserved amino acid (thus constituting the Cys-X-Cys or 'CXC' motif; see FIG. 1) and devoid of a three amino acid sequence, glutamic acid-leucine-arginine (the 'ELR' motif), immediately proximal to the CXC sequence. Examples of interferon-inducible (ELR−)CXC chemokines include human CXCL9 (SEQ ID NO: 1), murine CXCL9 (SEQ ID NO: 2), human CXCL10 (SEQ ID NO: 4), murine CXCL10 (SEQ ID NO: 5), human CXCL11 (SEQ ID NO: 7) and murine CXCL11 (SEQ ID NO: 8). CXCL9, CXCL10 and CXCL11 are potently induced by both type 1 and type 2 interferons (IFN-$\alpha/\beta$ and IFN-$\gamma$, respectively).

As used herein, the term "adjuvant" as used herein refers to an agent which enhances the pharmaceutical effect of another agent.

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, charged residues and their amides:
Asp, Asn, Glu, Gln, His, Arg, Lys;
III. Large, aliphatic, nonpolar residues:
Met Leu, Ile, Val, Cys
IV. Large, aromatic residues:
Phe, Tyr, Trp The term "antibody," as used herein, refers to an immunoglobulin molecule which is able to specifically bind to a specific epitope on an antigen. Antibodies can be derived from natural sources or from recombinant sources and may be intact immunoglobulins, or immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antimicrobial agent", as used herein, refers to any entity that exhibits antimicrobial activity, i.e. the ability to inhibit the growth and/or kill bacteria, including for example the ability to inhibit growth or reduce viability of bacteria by at least about 30%, at least about 40%, at least about 50%, at least about 60%, at least about 70% or more than 70%, as compared to bacteria not exposed to the antimicrobial agent. The antimicrobial agent can exert its effect either directly or indirectly and can be selected from a library of diverse compounds, including for example antibiotics. For example, various antimicrobial agents act, inter alia, by interfering with (1) cell wall synthesis, (2) plasma membrane integrity, (3) nucleic acid synthesis, (4) ribosomal function, and (5) folate synthesis. One of ordinary skill in the art will appreciate that a number of "antimicrobial susceptibility" tests can be used to determine the efficacy of a candidate antimicrobial agent.

As used herein, the term "antisense oligonucleotide" means a nucleic acid polymer, at least a portion of which is complementary to a nucleic acid which is present in a normal cell or in an affected cell. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No. 5,034,506; Nielsen et al., 1991, Science 254: 1497).

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, the term "biologically active fragments" or "bioactive fragment" of the polypeptides encompasses natural or synthetic portions of the full-length protein that are capable of specific binding to their natural ligand or of performing the function of the protein.

A "pathogenic" cell is a cell which, when present in a tissue, causes or contributes to a disease or disorder in the animal in which the tissue is located (or from which the tissue was obtained).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

The term "complex", as used herein in reference to proteins, refers to binding or interaction of two or more proteins. Complex formation or interaction can include such things as binding, changes in tertiary structure, and modification of one protein by another, such as phosphorylation.

A "compound", as used herein, refers to any type of substance or agent that is commonly considered a chemical, drug, or a candidate for use as a drug, as well as combinations and mixtures of the above. The term compound further encompasses molecules such as peptides and nucleic acids.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

The terms "formula" and "structure" are used interchangeably herein.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) *J. Mol. Biol.* 215:403-410) are available for determining sequence identity.

The term "inhibit," as used herein, refers to the ability of a compound or any agent to reduce or impede a described function or pathway. For example, inhibition can be by at least 10%, by at least 25%, by at least 50%, and even by at least 75%.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated" compound/moiety is a compound/moeity that has been removed from components naturally associated with the compound/moiety. For example, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "modulate", as used herein, refers to changing the level of an activity, function, or process. The term "modulate" encompasses both inhibiting and stimulating an activity, function, or process.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

A peptide encompasses a sequence of 2 or more amino acids wherein the amino acids are naturally occurring or synthetic (non-naturally occurring) amino acids.

The term "linked" or like terms refers to a connection between two entities. The linkage may comprise a covalent, ionic, or hydrogen bond or other interaction that binds two compounds or substances to one another.

As used herein the term "peptidomimetic" refers to a chemical compound having a structure that is different from the general structure of an existing peptide, but that functions in a manner similar to the existing peptide, e.g., by mimicking the biological activity of that peptide. Peptidomimetics typically comprise naturally-occurring amino acids and/or unnatural amino acids, but can also comprise modifications to the peptide backbone. For example a peptidomimetic may include one or more of the following modifications:

1. peptides wherein one or more of the peptidyl —C(O) NR— linkages (bonds) have been replaced by a non-peptidyl linkage such as a —CH2-carbamate linkage (—CH2OC(O)NR—), a phosphonate linkage, a —CH2-sulfonamide (—CH2-S(O)2NR—) linkage, a urea (—NHC (O)NH—) linkage, a —CH2-secondary amine linkage, an azapeptide bond (CO substituted by NH), or an ester bond (e.g., depsipeptides, wherein one or more of the amide (—CONHR—) bonds are replaced by ester (COOR) bonds) or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;

3. peptides wherein the C terminus is derivatized to —C(O)R2 where R2 is selected from the group consisting of C1-C4 alkoxy, and —NR3R4 where R3 and R4 are independently selected from the group consisting of hydrogen and C1-C4 alkyl;

4. modification of a sequence of naturally-occurring amino acids with the insertion or substitution of a non-peptide moiety, e.g. a retroinverso fragment.

The term "permeability," as used herein, refers to transit of fluid, cell, or debris between or through cells and tissues.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds," as used herein, is meant a compound which recognizes and binds a specific protein, but does not substantially recognize or bind other molecules in a sample, or it means binding between two or more proteins as in part of a cellular regulatory process, where said proteins do not substantially recognize or bind other proteins in a sample.

The term "standard," as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

As used herein an "amino acid modification" refers to a substitution, addition or deletion of an amino acid, and includes substitution with, or addition of, any of the 20 amino acids commonly found in human proteins, as well as unusual or non-naturally occurring amino acids. Commercial sources of unusual amino acids include Sigma-Aldrich (Milwaukee, Wis.), ChemPep Inc. (Miami, Fla.), and Genzyme Pharmaceuticals (Cambridge, Mass.). Unusual amino acids may be purchased from commercial suppliers, synthesized de novo, or chemically modified or derivatized from naturally occurring amino acids. Amino acid modifications include linkage of an amino acid to a conjugate moiety, such as a hydrophilic polymer, acylation, alkylation, and/or other chemical derivatization of an amino acid.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substitutions may be designed based on, for example, the model of Dayhoff, et al. (in Atlas of Protein Sequence and Structure 1978, Nat'l Biomed. Res. Found., Washington D.C.).

Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306-1310 (1990).

Embodiments

In accordance with one embodiment a method is provided for identifying anti-bacterial agents that operate through a similar mechanism of action as chemokines, more particularly of CXC10. In one embodiment the present disclosure is directed to identifying compounds that bind to FtsX, and more particularly to the extracellular domains of FtsX protein of E. coli or Bacillus anthracis. In accordance with one embodiment compounds that bind to the extracellular domains of Bacillus anthracis FtsX (SEQ ID NO: 10) are identified. In a further embodiment compounds are screened to identify compounds that bind to the peptide KVEQDVEIRVHIDPAAKEADQKKLEDD (SEQ ID NO: 18). Identified compounds that bind to FtsX are then screened for bactericidal activity.

In accordance with one embodiment a method is provided for identifying anti-bacterial agents that operate through a similar mechanism of action as chemokines, more particularly of CXC10 based on their different bactericidal activity against a bacterial strain modified to be deficient in pyruvate dehydrogenase complex (PDHC) relative to the parent strain. Optionally, compounds can be tested for their ability to bind FtsX either prior to analyzing their bactericidal activity or after analyzing their bactericidal activity.

In one embodiment a method for identifying anti-bacterial agents that operate through a similar mechanism of action as chemokines comprises contacting a standard bacterial strain, and a derivative of that standard bacterial strain, with a candidate compound, wherein the derivative strain is one that has been modified to differ from standard strain by a mutation that makes the strain pyruvate dehydrogenase complex (PDHC)-deficient. After contact with the candidate compound, both bacterial strains are cultured under conditions favorable for growth and compounds are identified that inhibit the growth of the standard bacterial strain to a greater extent than the derivative strain. In one embodiment compounds are selected that inhibit the standard strain by more than 2×, 3×, 5×, 10× or 50× relative to the inhibition obtained by contact of the candidate compound with the corresponding derivative strain that is pyruvate dehydrogenase complex (PDHC)-deficient. In accordance with one embodiment the bacterial strains used in the method is an E. coli or B. anthracis strain. In one embodiment the PDHC-deficient bacterial strain is a pyruvate dehydrogenase complex subunit deletion mutant selected from the group consisting of ΔaceE, ΔaceF, and ΔlpdA. In one embodiment the bacterial strain is E. coli, and the pyruvate dehydrogenase complex subunit deletion mutant is ΔaceE. In one embodiment the method of screening for anti-bacterial agents that operate through a similar mechanism of action as chemokines further comprises a step of identifying compounds that bind to FtsX, and more particularly to the B. anthracis FtsE/X complex. In one embodiment the candidate compounds are screened to identify compounds that bind to the peptide KVEQDVEIRVHIDPAAKEADQKKLEDD (SEQ ID NO: 18).

In accordance with one embodiment a method for identifying antimicrobial agents is provided wherein the method comprises contacting a standard E. coli strain, and a corresponding derivative E. coli strain, with a candidate compound, wherein the derivative E. coli strain is a pyruvate dehydrogenase complex (PDHC)-deficient derivative of the standard E. coli strain. The two strains are then separately cultured under conditions suitable for growth and compounds are selected based on identifying those compounds that inhibit the growth of the standard E. coli strain to a greater degree (e.g., 2×, 3×, 5× or 10×) than the inhibition of the PDHC-deficient E. coli derivatives. In one embodiment the identified compound is one that inhibits the standard E. coli growth by more than 2-fold relative to the inhibition of the compound on the growth of the corresponding PDHC-deficient E. coli derivative. In one embodiment the PDHC-deficient E. coli derivative is a pyruvate dehydrogenase complex subunit deletion mutant selected from the group consisting of ΔaceE, ΔaceF, and ΔlpdA. In one embodiment the PDHC-deficient E. coli derivative is a ΔaceE pyruvate dehydrogenase complex subunit deletion mutant. In one embodiment the method further comprises a step of screening the candidate compounds to identify compounds that bind FtsX, including either E. coli or B. anthracis FtsX. In one embodiment the method further comprises a step of screening the candidate compounds to identify compounds that bind to the B. anthracis FtsE/X complex. In one embodiment the method further comprises a step of screening the candidate compounds to identify compounds that bind the peptide KVEQDVEIRVHIDPAAKEADQKKLEDD (SEQ ID NO: 18).

The present disclosure is also directed to a method of neutralizing prokaryotic pathogenic organisms comprising the step of contacting said pathogenic organisms with a composition comprising one or more compounds identified by the disclosed method for identifying anti-bacterial agents that operate through a similar mechanism of action as chemokines.

In accordance with one embodiment compositions and methods are provided for neutralizing pathogenic organisms. More particularly, applicants have found that interferon-inducible ELR-CXC chemokines have efficacy against pathogenic bacteria including Bacillus anthracis. In accordance with one embodiment a composition is provided for neutralizing pathogenic bacteria in all growth phases including sporulated forms. The compositions can be formulated for treatment of external surfaces including hard surfaces such as, medical equipment and medical devices, or the compositions can be formulated for topical or internal administration to subjects, including humans.

In accordance with one embodiment a composition is provided comprising a non-native peptide, or a peptidomimetic derivative, comprising a sequence selected from the group consisting of SEQ ID NO: 3, SEQ ID NO: 6 and SEQ ID NO: 9 or a sequence that differs from SEQ ID NO: 3, SEQ ID NO: 6 or SEQ ID NO: 9 by 1, 2, 3, 4 or 5 amino acids. In one embodiment the peptide differs from SEQ ID NO: 3, SEQ ID NO: 6 or SEQ ID NO: 9 by 1, 2, 3, 4 or 5 conservative amino acid substitutions. In accordance with one embodiment a composition is provided comprising a peptide, or a peptidomimetic derivative, comprising a sequence selected from the group consisting of SEQ ID NO: 3, SEQ ID NO: 6 and SEQ ID NO: 9. In a further embodiment a composition is provided comprising a non-native peptide, or a peptidomimetic derivative thereof, comprising a sequence selected from the group consisting of SEQ ID NO: 6, SEQ ID NO: 13 or SEQ ID NO: 16.

In another embodiment the non-native peptide, or peptidomimetic derivative thereof, comprises a sequence selected from the group consisting of SEQ ID NO: 12, SEQ ID NO: 13 and SEQ ID NO: 14 or a sequence that differs from SEQ ID NO: 12, SEQ ID NO: 13 or SEQ ID NO: 14 by 1, 2, 3, 4 or 5 amino acids. In another embodiment the peptide, or peptidomimetic derivative, comprises a sequence selected from the group consisting of SEQ ID NO: 15, SEQ ID NO: 16 and SEQ ID NO: 17 or a sequence that differs from SEQ ID NO: 15, SEQ ID NO: 16 or SEQ ID NO: 17 by 1, 2, 3, 4 or 5 amino acids. In another embodiment a composition is provided comprising a non-native peptide, or a peptidomimetic derivative, comprising a sequence selected from the group consisting of SEQ ID NO: 1, SEQ ID NO: 4 or SEQ ID NO: 7, and in further embodiment the sequence comprises the amino acid sequence of SEQ ID NO: 4 or SEQ ID NO: 16, or a peptidomimetic derivative thereof.

In one embodiment a composition comprising an interferon-inducible (ELR-) CXC chemokine is provided wherein the chemokine comprises a peptidomimetic derivative or non-native peptide sequence selected from the group consisting of i) SEQ ID NO: 3 or SEQ ID NO: 6 or a peptide having at least 95% amino acid sequence identity with SEQ ID NO: 3 or SEQ ID NO: 6 or SEQ ID NO: 9. In a further embodiment the interferon-inducible (ELR-) CXC chemokine comprises a sequence of SEQ ID NO: 15 or SEQ ID NO: 16. In a further embodiment the interferon-inducible (ELR-) CXC chemokine comprises a peptide sequence that differs from SEQ ID NO: 4 by no more than 1, 2, 3, 4 or 5 amino acid modifications at one or more positions selected from amino acid positions 3, 4, 6, 7, 9, 13, 15, 19, 22, 25, 31, 34, 36, 37, 38, 41, 42, 44, 45, 46, 55, 56, 69, 70, 72, 81, 86, 89, 92 or 97. In one embodiment the amino acid modifications are amino acid substitution, and in one embodiment the substitutions are conservative amino acid substitutions.

In some embodiments, the peptide of the present disclosures comprises a non-native amino acid sequence which has at least 75%, 80%, 85%, 90% or 95% sequence identity to an amino acid sequence of SEQ ID NO: 3, SEQ ID NO: 6 or SEQ ID NO: 9, or a peptidomimetic derivative of SEQ ID NO: 3, SEQ ID NO: 6 or SEQ ID NO: 9. The statement that the peptide is a non-native is intended to exclude the native peptides of SEQ ID NO: 1, SEQ ID NO: 4 and SEQ ID NO: 7. In some embodiments, the peptide of the present disclosures comprises a non-native amino acid sequence which has at least 75%, 80%, 85%, 90% or 95% sequence identity to an amino acid sequence of SEQ ID NO: 15, SEQ ID NO: 16 or SEQ ID NO: 17, or peptidomimetic derivative of SEQ ID NO: 15, SEQ ID NO: 16 or SEQ ID NO: 17. In some embodiments, the peptide of the present disclosure comprises a non-native amino acid sequence which has at least 75%, 80%, 85%, 90% or 95% sequence identity to an amino acid sequence of SEQ ID NO: 1, SEQ ID NO: 4 or SEQ ID NO: 7, or a peptidomimetic derivative of SEQ ID NO: 1, SEQ ID NO: 4 or SEQ ID NO: 7. In some embodiments, the peptide of the present disclosure comprises an amino acid sequence which has at least a 90% amino acid sequence identity with SEQ ID NO: 1, SEQ ID NO: 4 or SEQ ID NO: 7, with the proviso that the peptide is not SEQ ID NO: 1, SEQ ID NO: 4 or SEQ ID NO: 7. In some embodiments, the peptide of the present disclosure comprises a non-native amino acid sequence which has at least a 95% amino acid sequence identity with SEQ ID NO: 1, SEQ ID NO: 2, SEQ ID NO: 4 or SEQ ID NO: 16. In some embodiments, the peptide of the present disclosure comprises a non-native amino acid sequence which has at least a 95% amino acid sequence identity with SEQ ID NO: 16.

In some embodiments, the peptide of the present disclosures comprises an amino acid sequence which has at least 95% sequence identity to an amino acid sequence of SEQ ID NO: 1, SEQ ID NO: 4 or SEQ ID NO: 7. In some embodiments, the peptide of the present disclosures comprises an amino acid sequence which is at least 70%, at least 80%, at least 85%, at least 90% or has greater than 95% sequence identity to SEQ ID NO: 4. In some embodiments, the amino acid sequence of the presently disclosed peptide which has the above-referenced % sequence identity is the full-length amino acid sequence of the presently disclosed peptide.

In one embodiment an antimicrobial composition is provided comprising two or more interferon-inducible (ELR-) CXC chemokines. In one embodiment the composition comprises a purified first peptide having the sequence of SEQ ID NO; 12 or SEQ ID NO: 15, and a purified second peptide having the sequence of SEQ ID NO: 13 or SEQ ID NO: 16. In one embodiment the composition comprises a non-native first peptide having the sequence of SEQ ID NO: 15, and a non-native second peptide having the sequence of SEQ ID NO: 16.

It is disclosed herein that bacterial pyruvate dehydrogenase E1, one component of the three-part bacterial pyruvate dehydrogenase complex, is a target of CXC chemokines. In one aspect, the chemokine is CXCL10. Therefore, the present invention provides compositions and methods useful for inhibiting gram-negative bacteria, treating infections of gram-negative bacteria in subjects in need thereof, and methods for identifying agents useful for treating gram-negative bacteria infections. The present invention provides, in one aspect, the use of CXCL10, and biologically active fragments and homologs thereof as anti-bacterial agents that act by targeting pyruvate dehydrogenase E1. In one aspect, similar chemokines are encompassed by the methods of the invention. In one aspect, a compound of the invention inhibits bacterial growth. In one aspect, a compound of the invention inhibits bacterial survival.

It is further contemplated that the antimicrobial interferon-inducible (ELR-) CXC chemokines or active antimicrobial agents having the same mechanism of action as disclosed herein may be used in combination with, or to enhance the activity of, other antimicrobial agents or antibiotics. In one embodiment a composition is provided comprising an interferon-inducible (ELR-) CXC chemokine and a second antimicrobial agent. In one embodiment the second antimicrobial agent is an antibiotic. Combinations of an interferon-inducible (ELR-) CXC chemokine peptide (or other compounds identified by the methods disclosed herein) with other agents may be useful to allow antibiotics to be used at lower doses responsive to toxicity concerns, to enhance the activity of antibiotics whose efficacy has been reduced or to effectuate a synergism between the components such that the combination is more effective than the sum of the efficacy of either component independently.

In some embodiments, the antimicrobial agent is a quinolone antimicrobial agent, including for example but not limited to, ciprofloxacin, levofloxacin, and ofloxacin, gatifloxacin, norfloxacin, lomefloxacin, trovafloxacin, moxifloxacin, sparfloxacin, gemifloxacin, pazufloxacin or variants or analogues thereof. In some embodiments, the second antimicrobial agent is ofloxacin or variants or analogues thereof.

In some embodiments, the second antimicrobial agent is an aminoglycoside antimicrobial agent, including for example but not limited to, amikacin, gentamycin, tobramycin, netromycin, streptomycin, kanamycin, paromomycin, neomycin or variants or analogues thereof. In some embodiments, the second antimicrobial agent is gentamicin or variants or analogues thereof.

In some embodiments, the second antimicrobial agent is a beta-lactam antibiotic antimicrobial agent, including for example but not limited to, penicillin, ampicillin, penicillin derivatives, cephalosporins, monobactams, carbapenems, beta-lactamase inhibitors or variants or analogues thereof. In some embodiments, the second antimicrobial agent is ampicillin or variants or analogues thereof. In accordance with one embodiment the second antimicrobial agent is selected from a group consisting of penicillin, ampicillin, penicillin derivatives, cephalosporins, monobactams, carbapenems, or beta-lactamase inhibitors.

The compositions disclosed herein may include additional components that enhance their efficacy based on their desired use. In one embodiment the compositions are formulated as a pharmaceutical composition. The pharmaceutical compositions can be prepared for systemic (parenteral), inhalational (or inhaled), and topical applications using formulations and techniques known to those skilled in the art. Such pharmaceutical composition include one or more isolated or purified interferon-inducible (ELR-) CXC chemokines, or pharmaceutically acceptable salts thereof, and a pharmaceutically acceptable carrier. The pharmaceutical composition can comprise any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

In one embodiment the interferon-inducible (ELR-) CXC chemokine may be coupled, bonded, bound, conjugated, or chemically-linked to one or more agents via linkers, polylinkers, or derivatized amino acids. In accordance with one embodiment the composition further comprises a lipid vesicle delivery vehicle. In one embodiment the lipid vesicle is a liposome or micelle. Suitable lipids for liposomal and/or micelle formulation include, without limitation, monoglycerides, diglycerides, sulfatides, lysolecithin, phospholipid, saponin, bile acids, and the like. The preparation of liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, the disclosures of which are incorporated herein by reference. In accordance with one embodiment a composition is provided comprising an interferon-inducible (ELR-) CXC chemokine and a lipid vesicle, wherein the interferon-inducible (ELR-) CXC chemokine is encapsulated within the lipid vesicle, or linked to the surface of said lipid vesicle. In a further embodiment the composition may include additional active agents encapsulated or linked to the surface of the lipid vesicle delivery vehicle, including for example an anti-microbial agent such as an antibiotic. In one embodiment the lipid vesicle is a liposome, and in a further embodiment the liposome comprises interferon-inducible (ELR-) CXC chemokines linked to the exterior surface of the liposome. In one embodiment the interferon-inducible (ELR-) CXC chemokines are covalently bound to the exterior surface of the liposome, optionally with additional active antimicrobial agents encapsulated within or linked to the exterior surface of the liposome.

In some embodiments, the pharmaceutical composition comprises an interferon-inducible (ELR-) CXC chemokine and an antibiotic. Antibiotics suitable for use in accordance with the present description include for example, but are not limited to, an antibiotic (e.g. nisin or epidermin), almecillin, amdinocillin, amikacin, amoxicillin, amphomycin, amphotericin B, ampicillin, azacitidine, azaserine, azithromycin, azlocillin, aztreonam; bacampicillin, bacitracin, benzyl penicilloyl-polylysine, bleomycin, candicidin, capreomycin, carbenicillin, cefaclor, cefadroxil, cefamandole, cefazoline, cefdinir, cefepime, cefixime, cefinenoxime, cefinetazole, cefodizime, cefonicid, cefoperazone, ceforanide, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, chlortetracycline, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), dactinomycin, dalbavancin, dalfopristin, daptomycin, daunorubicin, demeclocycline, detorubicin, dicloxacillin, dihydrostreptomycin, dirithromycin, doxorubicin, doxycycline, epirubicin, erythromycin, eveninomycin, floxacillin, fosfomycin, fusidic acid, gemifloxacin, gentamycin, gramicidin, griseofulvin, hetacillin, idarubicin, imipenem, iseganan, ivermectin, kanamycin, laspartomycin, linezolid, linocomycin, loracarbef, magainin, meclocycline, meropenem, methacycline, methicillin, mezlocillin, minocycline, mitomycin, moenomycin, moxalactam, moxifloxacin, mycophenolic acid, nafcillin, natamycin, neomycin, netilmicin, niphimycin, nitrofurantoin, novobiocin, oleandomycin, oritavancin, oxacillin, oxytetracycline, paromomycin, penicillamine, penicillin G, penicillin V, phenethicillin, piperacillin, plicamycin, polymyxin B, pristinamycin, quinupristin, rifabutin, rifampin, rifamycin, rolitetracycline, sisomicin, spectrinomycin, streptomycin, streptozocin, sulbactam, sultamicillin, tacrolimus, tazobactam, teicoplanin, telithromycin, tetracycline, ticarcillin, tigecycline, tobramycin, troleandomycin, tunicamycin, tyrthricin, vancomycin, vidarabine, viomycin, virginiamycin, BMS-284,756, L-749,345, ER-35,786, S-4661, L-786,392, MC-02479, Pep5, RP 59500, and TD-6424. In some embodiments, two or more antimicrobial agents (e.g., a composition comprising an interferon-inducible (ELR-) CXC chemokine and an antibiotic) may be used together or sequentially. In some embodiments, another antibiotic may comprise bacteriocins, type A lantibiotics, type B lantibiotics, liposidomycins, mureidomycins, alanoylcholines, quinolines, eveninomycins, glycylcyclines, carbapenems, cephalosporins, streptogramins, oxazolidonones, tetracyclines, cyclothialidines, bioxalomycins, cationic peptides, and/or protegrins.

In one embodiment the antibiotics that are combined with the interferon-inducible (ELR−) CXC chemokine include but are not limited to penicillin, ampicillin, amoxycillin, vancomycin, cycloserine, bacitracin, cephalolsporin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraminosalicylic acid, and ethambutol. In some embodiments, the antibiotic comprises one or more anti-anthrax agents (e.g., an antibiotic used in the art for treating *B. anthracis* (e.g., penicillin, ciprofloxacin, doxycycline, erythromycin, and vancomycin)).

In one embodiment a kit is provided for neutralizing pathogenic organisms. In one embodiment the kit comprises an interferon-inducible (ELR−) CXC chemokine as disclosed herein and additional known antimicrobial agents, including one or more antibiotics. In a further embodiment the kit comprises a type 1 and/or type 2 interferons (e.g., IFN-α/β and IFN-γ, respectively).

Neutralizing Stationary Phase Bacteria

Many antibiotics are only poorly effective against non-growing or stationary phase bacteria. During the stationary period bacterial cells frequently have a thicker peptidoglycan cell wall and typically have differences in protein metabolism. Many complications that arise during the course of treating bacterial infections are due to stationary phase or dormant bacteria which as noted above resist conventional antibiotic treatments. The formation of biofilms on temporary (e.g., catheters) or more permanent implants and the colonizations seen in patients afflicted with certain diseases cannot be effectively treated with the antimicrobial agents currently available. In terms of bacterial colonization and diseases that can arise from it, the airways and the GI tract are the major areas affected. The presence of inappropriate bacterial colonizations is believed to cause complications associated with inflammatory bowel diseases (including ulcerative colitis and Crohn's disease) and irritable bowel syndrome. In addition with regards to the airways alone, the major diseases that can arise from or can be exacerbated by bacterial colonization include: sinus infections, respiratory infections such as pneumonia (this is especially applicable to ventilator-associated pneumonias but also applies to community-acquired pneumonias), chronic obstructive pulmonary disease (COPD), and cystic fibrosis (CF).

Surprisingly, applicants have discovered that the interferon-inducible (ELR−) CXC chemokines have activity in neutralizing stationary phase bacteria as well as actively growing bacteria. In accordance with one embodiment a method is provided for neutralizing prokaryotic pathogenic organisms that have colonized a host organism and have entered into a stationary growth phase. It is also anticipated that the interferon-inducible (ELR−) CXC chemokine containing compositions may have efficacy in neutralizing biofilms. The method comprises the step of contacting the pathogenic organisms with a composition comprising an interferon-inducible (ELR−) CXC chemokine.

In accordance with one embodiment the method comprises the steps of contacting the pathogenic organisms with an effective amount of a peptide selected from the group consisting of i) CXCL-9 (SEQ ID NO: 1), CXCL-10 (SEQ ID NO: 4) or CXCL 11 (SEQ ID NO: 7), ii) a peptide fragment of CXCL-9, CXCL-10 or CXCL 11, or a peptide having at least 90% amino acid sequence identity with i) or ii). In one embodiment the peptide comprises the sequence of SEQ ID NO: 3, SEQ ID NO: 6 and SEQ ID NO: 9, or a peptidomimetic derivative thereof. In another embodiment the peptide comprises a sequence selected from the group consisting of i) SEQ ID NO: 3 or SEQ ID NO: 6 or a peptide having at least 95% amino acid sequence identity with SEQ ID NO: 3 or SEQ ID NO: 6 or SEQ ID NO: 9. In one embodiment the peptide comprises the sequence of SEQ ID NO: 15 or SEQ ID NO: 16. In another embodiment the peptide comprises a peptide sequence that differs from SEQ ID NO: 4 by no more than 1, 2, 3, 4 or 5 amino acid modifications at positions selected from amino acid positions 3, 4, 6, 7, 9, 13, 15, 19, 22, 25, 31, 34, 36, 37, 38, 41, 42, 44, 45, 46, 55, 56, 69, 70, 72, 81, 86, 89, 92 or 97. In one embodiment the amino acid modifications are amino acid substitutions including for example conservative amino acid substitutions.

Since interferons are known to induce expression of native CXCL9, CXCL10 and CXCL11, in one embodiment the method of treatment comprises the co-administration of one or more interferons, including for example interferon-alpha, interferon-beta and/or interferon-gamma as an adjuvant to promote production of native CXCL9, CXCL10 and CXCL11 chemokines in vivo. Co-administration can be accomplished by simultaneously administering the chemokine and the interferon, or the two active agents can be administered one after the other within 1, 2, 3, 4, 5, 6, 12, 24 or 48 hours of each other.

The pathogenic organisms are placed in contact using an appropriate route of administration. For example, for treating skin, the composition can be formulated as a topical cream or in a rinsing solution. Such composition can be used sterilize external body parts that may have come in contact with pathogenic organisms such as *Bacillus anthracis*. Alternatively, formulations for oral administration can be prepared for treating bacterial colonization of the the digestive tract. In another embodiment the composition can be formulated as an aerosol for administration to the lungs and air pathways of a subject. Such formulations can be prepared using standard formulations and techniques known to the skilled practitioner.

The interferon-inducible (ELR−) CXC chemokine compositions will be administered in an amount effective to neutralize the bacteria. An "effective" amount or a "therapeutically effective amount" of the interferon-inducible (ELR−) CXC chemokine refers to a nontoxic but sufficient amount of the compound to provide the desired effect. The amount that is "effective" will vary based on the organism to be neutralized, whether an external surface is to be treated or whether the composition is to be administered as a pharmaceutical, the mode of administration, and the like. Thus, it is not always possible to specify an exact "effective amount." However, an appropriate "effective" amount in any individual case may be determined by one of ordinary skill in the art using routine experimentation. In one embodiment the method comprises contacting the bacteria with an interferon-inducible (ELR−) CXC chemokine at a concentration of about 1 to about 50 µg/ml, 1 to about 30 µg/ml, 1 to about 15 µg/ml, 2 to about 10 µg/ml, 4 to about 8 µg/ml, 6 to about 10 µg/ml or about 8 µg/ml. Typically the bacteria are contacted with an effective amount of the interferon-inducible (ELR−) CXC chemokines for a time ranging from 1 to 6, 2 to 8, 4 to 12 or 12 to 24 hours.

In accordance with one embodiment the administered anti-microbial composition comprises an interferon-inducible (ELR−) CXC chemokine having a peptide sequence selected from the group consisting of SEQ ID NO: 3, SEQ ID NO: 6 and SEQ ID NO: 9, or a peptidomimetic derivative thereof. In one embodiment such a composition is used to neutralize and/or kill both active and stationary phase pathogenic bacteria, including for example pathogenic organism is selected from the group consisting of *Streptococcus pneumoniae, Staphylococcus aureus, Moraxella catarrhalis, Hemophilus influenzae, Enterobacteriaceae, Pseudomonas aeruginosa, Stenotrophomonas maltophilia, Streptococcus viridans, Neisseria* spp., and *Corynebacterium* spp.

Several disease states are associated with large populations of stationary phase bacteria, and currently there are not effective treatments for removing such bacterial colonizations of patients. These diseases include pneumonia (this is especially applicable to ventilator-associated pneumonias but also applies to community-acquired pneumonias), and pulmonary infections associated with, chronic obstructive pulmonary disease (COPD), cystic fibrosis (CF), wherein populations of bacteria remain resident in the host organism. Major contributors to pathogenic infections of patient airways include both Gram-positive and Gram-negative bacteria and include, but are not limited to the following as major contributors Gram-positive cocci such as *Streptococcus pneumoniae* and *Staphylococcus aureus* Gram-negative cocci such as *Moraxella catarrhalis* Gram-negative rods such as *Hemophilus influenzae, Enterobacteriaceae*, and *Pseudomonas aeruginosa*. Additional organisms that might play a role in immunocompromised hosts (in addition to the above listed organisms) may include *Streptococcus viridans* group, coagulase-negative staphylococci, *Neisseria* spp., *Corynebacterium* spp. Yeast such as *Candida* spp. can also play a role. In cystic fibrosis patients, *Stenotrophomonas maltophilia* is an ever more problematic Gram negative pathogen that colonizes the airways along with the above listed organisms (especially *Pseudomonas aeruginosa* and *S. aureus*). One aspect of the present disclosure is the use of the interferon-inducible (ELR−) CXC chemokines to treat subjects suffering from a disease or condition that is exacerbated by the presence of inappropriate bacteria.

In accordance with one embodiment the method of treating a pathogenic colonization of a patient is provided wherein a composition comprising an interferon-inducible (ELR−) CXC chemokine peptide, or peptidomimetic derivative thereof is administered to the patient. In one embodiment the composition comprises a peptide selected from the group i) SEQ ID NO: 1, SEQ ID NO: 2, SEQ ID NO: 4 SEQ ID NO: 5, SEQ ID NO: 7 and SEQ ID NO: 8, ii) a peptide fragment of SEQ ID NO: 1, SEQ ID NO: 2, SEQ ID NO: 4, SEQ ID NO: 5, SEQ ID NO: 7 and SEQ ID NO: 8, or a peptide having at least 90% amino acid sequence identity with i) or ii). In a further embodiment the composition comprises an interferon-inducible (ELR−) CXC chemokine peptide, or peptidomimetic derivative thereof, wherein the peptide comprises a sequence selected from the group consisting of SEQ ID NO: 1, SEQ ID NO: 2 and SEQ ID NO: 4. In a further embodiment the composition comprises two or three peptides selected from the group consisting of SEQ ID NO: 1, SEQ ID NO: 2, and SEQ ID NO: 4. In one embodiment the composition comprises a peptide comprising the sequence of SEQ ID NO: 1, SEQ ID NO: 2 and SEQ ID NO: 4 or a sequence that is 95% identical in sequence with SEQ ID NO: 1, SEQ ID NO: 2 or SEQ ID NO: 4. In accordance with one embodiment the composition comprises the sequence of SEQ ID NO: 4 or a sequence that differs from SEQ ID NO: 4 by 1, 2, 3, 4, 5, 6, 7, 8, 9, or 10 amino acids at positions independently selected from positions 4, 7, 22, 25, 37, 44, 45, 72, 86, 91, 92, 97. In one embodiment the differences represent conservative amino acid substitutions.

In one embodiment the compositions further comprise additional anti-microbial agents including for example one or more antibiotics. In another embodiment the method comprises administering one or more interferon-inducible (ELR−) CXC chemokine peptides wherein the interferon-inducible (ELR−) CXC chemokine is linked, optionally via covalent bonding and optionally via a linker, to a conjugate moiety. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The peptide can be linked to conjugate moieties via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the peptide indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Exemplary conjugate moieties that can be linked to any of the glucagon peptides described herein include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents.

In accordance with one embodiment a method of treating a pathogenic colonization of a patient is provided wherein a composition comprising the interferon-inducible (ELR−) CXC chemokine linked to a lipid vesicle is administered to a subject in need thereof. In one embodiment the interferon-inducible (ELR−) CXC chemokine is linked to the external surface of the lipid vesicle, and in one embodiment the interferon-inducible (ELR−) CXC chemokine is covalently bound to the lipids comprising the lipid vesicle. In an alternative embodiment the interferon-inducible (ELR−) CXC chemokine is entrapped within the lipid vesicle. In one embodiment the lipid vesicle is a liposome. In a further embodiment the composition comprises additional anti-microbial agents, including for example one or more antibiotics. It is anticipated that the administration of the interferon-inducible (ELR−) CXC chemokine will enhance the efficacy of the known anti-microbial agent. The known anti-microbial agents can be co-administered with the interferon-inducible (ELR−) CXC chemokine either in a single dosage form or the therapeutic agents can be administered sequentially, within 5, 10, 15, 30, 60, 120, 180, 240 minutes or 12, 24 or 48 hours, to one another. In one embodiment the known anti-microbial agents are linked to a liposome, optionally with the interferon-inducible (ELR–) CXC chemokine also linked to the same liposome.

Neutralizing Multi-Drug Resistant Strains

During the last several decades bacterial resistance has emerged as a new trend, contributing to morbidity and mortality caused by bacterial infections. A troubling percentage of all infections encountered in clinical settings are resistant to some form of antibiotic therapy. Due to the excessive and not always appropriate use of antibiotics in humans and animal feed, bacterial resistance currently constitutes a major public health crisis. The World Health Organization (WHO) reported that drug resistant strains of microbes had a negative impact on their fight against tuberculosis, cholera, diarrhea and pneumonia, which together killed more than ten million people worldwide in 1995.

Multi-drug resistant strains of bacteria such as methicillin-resistant Staphylococcal aureus (MRSA) and vancomycin-resistant enterococci (VRE) were first encountered in hospital settings, but many of them can now be found infecting healthy individuals in larger communities. The spread of VRE is particularly concerning when it is taken into account that vancomycin is generally regarded as the last line of defense in the antibiotic arsenal. Additionally, the extensive use of beta-lactam antibiotics such as penicillin and ampicillin has also resulted in significant numbers of resistant strains among both Gram-positive and Gram-negative bacteria. Furthermore, strains can be deliberately engineered to have multi-drug resistance as part of "weaponization" of wild type strains, including for example *Bacillus anthracis*.

Currently, the choices for treatment of antibiotic-resistant and multi-drug resistant bacteria are limited in scope even though the molecular mechanisms of resistance are fairly well understood. The four main mechanisms by which microorganisms exhibit resistance to antimicrobials are:

1) Drug inactivation or modification: e.g. enzymatic deactivation of Penicillin G in some penicillin-resistant bacteria through the production of β-lactamases.

2) Alteration of target site: e.g. alteration of PBP—the binding target site of penicillins—in MRSA and other penicillin-resistant bacteria.

3) Alteration of metabolic pathway: e.g. some sulfonamide-resistant bacteria do not require para-aminobenzoic acid (PABA), an important precursor for the synthesis of folic acid and nucleic acids in bacteria inhibited by sulfonamides. Instead, like mammalian cells, they turn to utilizing preformed folic acid.

4) Reduced drug accumulation: by decreasing drug permeability and/or increasing active efflux (pumping out) of the drugs across the cell surface. In many cases, antibiotic-resistant and multi-drug resistant bacteria such as MRSA and VRE encode the antibiotic resistance genes on plasmids. These plasmids can be laterally transferred between bacteria and hence account for the rapid dissemination of antibiotic resistance genes into diverse bacterial populations.

Surprisingly, applicants have found that compositions comprising the Interferon-inducible (ELR–) CXC chemokines disclosed herein have efficacy in neutralizing multi-drug resistant bacteria. Accordingly, one aspect of the present disclosure is the use of the Interferon-inducible (ELR–) CXC chemokines either alone or in combination with other antimicrobial agents to neutralized multi-drug resistant bacteria. In one embodiment a method for inhibiting the proliferation of multi-drug resistant bacteria comprises contacting a multi-drug resistant cell with an effective amount of the compound of an interferon-inducible (ELR–) CXC chemokine of the present disclosure.

In accordance with one embodiment the method comprises the steps of contacting the multi-drug resistant organisms with an effective amount of a peptide selected from the group consisting of i) CXCL-9 (SEQ ID NO: 1), CXCL-10 (SEQ ID NO: 4) or CXCL 11 (SEQ ID NO: 7), ii) a peptide fragment of CXCL-9, CXCL-10 or CXCL 11, or a peptide having at least 90% amino acid sequence identity with i) or ii). In one embodiment the peptide comprises the sequence of SEQ ID NO: 3, SEQ ID NO: 6 and SEQ ID NO: 9, or a peptidomimetic derivative thereof. In another embodiment the peptide comprises a sequence selected from the group consisting of i) SEQ ID NO: 3 or SEQ ID NO: 6 or a peptide having at least 95% amino acid sequence identity with SEQ ID NO: 3 or SEQ ID NO: 6 or SEQ ID NO: 9. In one embodiment the peptide comprises the sequence of SEQ ID NO: 15 or SEQ ID NO: 16. In a further embodiment the multi-drug resistant organisms are contacted with a composition comprising an interferon-inducible (ELR–) CXC chemokine peptide, or peptidomimetic derivative thereof, wherein the peptide comprises a sequence selected from the group consisting of SEQ ID NO: 1, SEQ ID NO: 2 and SEQ ID NO: 4. In a further embodiment the composition comprises two or three peptides selected from the group consisting of SEQ ID NO: 1, SEQ ID NO: 2, and SEQ ID NO: 4. In one embodiment the composition comprises a peptide comprising the sequence of SEQ ID NO: 1, SEQ ID NO: 2 and SEQ ID NO: 4 or a sequence that is 95% identical in sequence with SEQ ID NO: 1, SEQ ID NO: 2 or SEQ ID NO: 4. In another embodiment the peptide comprises a peptide sequence that differs from SEQ ID NO: 4 by no more than 1, 2, 3, 4 or 5 amino acid modifications at positions selected from amino acid positions 3, 4, 6, 7, 9, 13, 15, 19, 22, 25, 31, 34, 36, 37, 38, 41, 42, 44, 45, 46, 55, 56, 69, 70, 72, 81, 86, 89, 92 or 97. In one embodiment the amino acid modifications are amino acid substitutions including for example conservative amino acid substitutions.

In one embodiment the method comprises contacting the bacteria with an interferon-inducible (ELR–) CXC chemokine at a concentration of about 1 to about 50 µg/ml, 1 to about 30 µg/ml, 1 to about 15 µg/ml, 2 to about 10 µg/ml, 4 to about 8 µg/ml, 6 to about 10 µg/ml or about 8 µg/ml.

Since interferons are known to induce expression of native CXCL9, CXCL10 and CXCL11, in one embodiment the method of treatment comprises the co-administration to a subject in need thereof one or more interferons, including for example interferon-alpha, interferon-beta and/or interferon-gamma as an adjuvant to promote production of native CXCL9, CXCL10 and CXCL11 chemokines in vivo. Co-administration can be accomplished by simultaneously administering the chemokine and the interferon, or the two active agents can be administered one after the other within 1, 2, 3, 4, 5, 6, 12, 24 or 48 hours of each other.

Neutralizing Bacterial Spores

Spores are resistant to most agents that would normally kill the vegetative cells they formed from. Household cleaning products generally have no effect, nor do most alcohols, quaternary ammonium compounds or detergents. Currently, treatments are not available that are designed to decontaminate (e.g., neutralize and/or prevent the growth or germination of) spores on human skin or other human surfaces (e.g., lungs or hair). Thus, there is a need for compositions and methods that can neutralize and prevent the outgrowth of spores of pathogenic bacteria such as *Bacillus anthracis*. Such an agent would ideally be easily disseminated, not be harmful to human surfaces (e.g., skin or lungs) and would be capable of altering (e.g., inhibiting) spore germination and growth potential (e.g., thereby leaving the spores inert and non-infectious).

Surprisingly, applicants have discovered that Interferon-inducible (ELR−) CXC chemokines are effective in neutralizing spores. Specifically, recombinant CXCL9, CXCL10, and CXCL11 exhibit direct inhibitory effects on spore germination and directly kill vegetative cells of *B. anthracis*. Selective in vivo neutralization of CXCL9 or CXCL9/CXCL10, or CXCL9/CXCL10/CXCL11 rendered normally resistant C57BU6 mice susceptible to pulmonary anthrax whereas neutralization of their shared receptor, CXCR3 (i.e., the common receptor expressed on leukocytes recruited to the site of infection by CXCL9, CXCL10, CXCL11), had no impact on survival. These findings support the notion that Interferon-inducible (ELR−) CXC chemokines have direct antimicrobial effects against *B. anthracis* in vitro and during in vivo infection.

In accordance with one embodiment a method of neutralizing spores, particularly of pathogenic bacteria such as *B. anthracis* and *C. difficile* is provided, wherein the method comprises contacting the spores with a composition comprising an interferon-inducible (ELR−) CXC chemokine. In accordance with one embodiment the method comprises the steps of contacting the spores with an effective amount of a peptide selected from the group consisting of i) CXCL-9 (SEQ ID NO: 1), CXCL-10 (SEQ ID NO: 4) or CXCL 11 (SEQ ID NO: 7), ii) a peptide fragment of CXCL-9, CXCL-10 or CXCL 11, or a peptide having at least 90% amino acid sequence identity with i) or ii). In one embodiment the peptide comprises the sequence of SEQ ID NO: 3, SEQ ID NO: 6 and SEQ ID NO: 9, or a peptidomimetic derivative thereof.

In another embodiment the peptide comprises a sequence selected from the group consisting of i) SEQ ID NO: 3 or SEQ ID NO: 6 or a peptide having at least 95% amino acid sequence identity with SEQ ID NO: 3 or SEQ ID NO: 6 or SEQ ID NO: 9. In one embodiment the peptide comprises the sequence of SEQ ID NO: 15 or SEQ ID NO: 16. In a further embodiment the spores are contacted with a composition comprising an interferon-inducible (ELR−) CXC chemokine peptide, or peptidomimetic derivative thereof, wherein the peptide comprises a sequence selected from the group consisting of SEQ ID NO: 1, SEQ ID NO: 2 and SEQ ID NO: 4. In a further embodiment the composition comprises two or three peptides selected from the group consisting of SEQ ID NO: 1, SEQ ID NO: 2, and SEQ ID NO: 4. In one embodiment the composition comprises a peptide comprising the sequence of SEQ ID NO: 1, SEQ ID NO: 2 and SEQ ID NO: 4 or a sequence that is 95% identical in sequence with SEQ ID NO: 1, SEQ ID NO: 2 or SEQ ID NO: 4. In another embodiment the peptide comprises a peptide sequence that differs from SEQ ID NO: 4 by no more than 1, 2, 3, 4 or 5 amino acid modifications at positions selected from amino acid positions 3, 4, 6, 7, 9, 13, 15, 19, 22, 25, 31, 34, 36, 37, 38, 41, 42, 44, 45, 46, 55, 56, 69, 70, 72, 81, 86, 89, 92 or 97. In one embodiment the amino acid modifications are amino acid substitutions including for example conservative amino acid substitutions.

The present invention is not limited by the type of bacterial spore neutralized. In some embodiments, the spore is a *Bacillus* spore, including for example a *Bacillus anthracis* spore. The *Bacillus anthracis* spore may be a naturally occurring spore or a genetically or mechanically engineered form. The spore may also be from an antibiotic resistant strain of *B. anthracis* (e.g., ciprofloxacin resistant). In some embodiments, the interferon-inducible (ELR−) CXC chemokine is administered to a subject under conditions such that spore germination or growth is prohibited and/or attenuated. In some embodiments, greater than 70%, 80%, or 90% of bacterial spores are neutralized (e.g., killed). In some embodiments, there is greater than 2 log (e.g., greater than 3 log, 4 log, 5 log, . . . ) reduction in bacterial spore outgrowth. In some embodiments, reduction in spore outgrowth occurs within hours (e.g., with 1 hour (e.g., in 20-40 minutes or less), within 2 hours, within 3 hours, within 6 hours or within 12 hours). In some embodiments, neutralization of the spore (e.g., the inability of the spore to germinate) lasts for at least 3 days, at least 7 days, at least 14 days, at least 21 days, at least 28 days, or at least 56 days.

In one embodiment the method comprises contacting the spores with an interferon-inducible (ELR−) CXC chemokine at a concentration of about 1 to about 50 µg/ml, 1 to about 30 µg/ml, 1 to about 15 µg/ml, 2 to about 10 µg/ml, 4 to about 8 µg/ml, 6 to about 10 µg/ml or about 8 µg/ml.

Surprisingly, applicants have found that the Interferon-inducible (ELR−) CXC chemokines have activity in neutralizing spores under physiological conditions. In accordance with one embodiment a method is provided for neutralizing spores of a prokaryotic pathogenic organism. The method comprises contacting the spores with a composition comprising an interferon-inducible (ELR−) CXC chemokine. In accordance with one embodiment a method is provided for neutralizing spores from an organism selected from the group consisting of *Bacillus anthracis*, *Bacillus cereus*, *Clostridium difficile*, *Clostridium botulinum*, *Clostridium perfringens*, *Clostridium tetani* and *Clostridium sordellii*. In one embodiment the method comprises neutralizing spores from an organism selected from the group consisting of *Bacillus anthracis* and *Clostridium difficile*, and in one specific embodiment the method comprises neutralizing *Bacillus anthracis* spores.

In one embodiment the method comprises contacting the spores with a composition comprising an interferon-inducible (ELR−) CXC chemokine having a peptide sequence selected from the group consisting of SEQ ID NO: 3, SEQ ID NO: 6 and SEQ ID NO: 9, or a peptidomimetic derivative thereof. In another embodiment the spores are contacted with an interferon-inducible (ELR−) CXC chemokine having a peptide sequence selected from the group consisting of i) SEQ ID NO: 1, SEQ ID NO: 2, SEQ ID NO: 4 SEQ ID NO: 5, SEQ ID NO: 7 and SEQ ID NO: 8, ii) a peptide fragment of SEQ ID NO: 1, SEQ ID NO: 2, SEQ ID NO: 4, SEQ ID NO: 5, SEQ ID NO: 7 and SEQ ID NO: 8, or a peptide having at least 90% amino acid sequence identity with i) or ii). In a further embodiment the composition comprises an interferon-inducible (ELR−) CXC chemokine peptide, or peptidomimetic derivative thereof, wherein the peptide comprises a sequence selected from the group consisting of SEQ ID NO: 1, SEQ ID NO: 2, SEQ ID NO: 4 and SEQ ID NO: 7. In a further embodiment the composition comprises two or three peptides selected from the group consisting of SEQ ID NO: 1, SEQ ID NO: 2, SEQ ID NO: 4 and SEQ ID NO: 7. In one embodiment the composition comprises a peptide comprising the sequence of SEQ ID NO: 1, SEQ ID NO: 2, SEQ ID NO: 4 and SEQ ID NO: 7 or a sequence that is 95% identical in sequence with SEQ ID NO: 1, SEQ ID NO: 2, SEQ ID NO: 4 and SEQ ID NO: 7. In accordance with one embodiment the composition comprises the sequence of SEQ ID NO: 4 or a sequence that differs from SEQ ID NO: 4 by 1, 2, 3, 4, 5, 6, 7, 8, 9, or 10 amino acids at positions independently selected from positions 4, 7, 22, 25, 37, 44, 45, 72, 86, 91, 92, 97. In one embodiment the differences represent conservative amino acid substitutions.

Since interferons are known to induce expression of native CXCL9, CXCL10 and CXCL11, in one embodiment the method of treatment comprises the co-administration to a subject in need thereof one or more interferons, including for example interferon-alpha, interferon-beta and/or interferon-gamma as an adjuvant to promote production of native CXCL9, CXCL10 and CXCL11 chemokines in vivo. Co-administration can be accomplished by simultaneously administering the chemokine and the interferon, or the two active agents can be administered one after the other within 1, 2, 3, 4, 5, 6, 12, 24 or 48 hours of each other.

In one embodiment the compositions further comprise additional anti-microbial agents including for example one or more antibiotics. In another embodiment the method comprises administering one or more interferon-inducible (ELR-) CXC chemokine peptides wherein the interferon-inducible (ELR-) CXC chemokine is linked, optionally via covalent bonding and optionally via a linker, to a conjugate moiety. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

In accordance with one embodiment the interferon-inducible (ELR-) CXC chemokine compositions disclosed herein are used to treat solid surfaces to neutralize spore contaminated surfaces. In one embodiment the compositions disclosed herein are used to decontaminate organic materials including food or the external surfaces of animals including human skin. In another embodiment the methods for neutralizing spores comprises administering a pharmaceutical composition comprising an interferon-inducible (ELR-) CXC chemokine to neutralize spores that have been internalized by a subject. In one embodiment the composition is formulated as an aerosol or other formulation known to those skilled in the art for administration to pulmonary system. In one embodiment the composition is formulated for oral delivery using formulations known to those skilled in the art for administration to the digestive tract.

Methods of Identifying Antagonists and Inhibitors of FtsX

As used herein, an antagonist or inhibiting agent may comprise, without limitation, a drug, a small molecule, an antibody, an antigen binding portion thereof or a biosynthetic antibody binding site that binds a particular target protein; an antisense molecule that hybridizes in vivo to a nucleic acid encoding a target protein or a regulatory element associated therewith, or a ribozyme, aptamer, a phylomer or small molecule that binds to and/or inhibits a target protein, or that binds to and/or inhibits, reduces or otherwise modulates expression of nucleic acid encoding a target protein, including for example RNA interference (e.g., use of small interfering RNA (siRNA)).

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other proteins. Such screening assays will include assays amenable to high-throughput screening of chemical libraries, making them particularly suitable for identifying small molecule drug candidates.

FtsX assays also include those described in detail herein, such as far-western, co-immunoprecipitation, immunoassays, immunocytochemical/immunolocalization, interaction with FtsX protein, fertilization, contraception, and immunogenicity.

The assays can be performed in a variety of formats, including protein-protein binding assays, biochemical screening assays, high-throughput assays, immunoassays, and cell-based assays, which are well characterized in the art.

All assays for antagonists are common in that they call for contacting the compound or drug candidate with a peptide identified herein under conditions and for a time sufficient to allow these two components to interact.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with, but does not bind to a particular peptide identified herein, its interaction with that peptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991). Complete kits for identifying protein-protein interactions between two specific proteins using the two-hybrid technique are available. This system can also be extended to map protein domains involved in specific protein interactions as well as to pinpoint amino acid residues that are crucial for these interactions.

Compounds that interfere with the interaction of a peptide identified herein and other intra- or extracellular components can be tested as follows: usually a reaction mixture is prepared containing the product of the gene and the intra- or extracellular component under conditions and for a time allowing for the interaction and binding of the two products.

To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the peptide may be added to a cell along with the compound to be screened for a particular activity and the ability of the compound to inhibit the activity of interest in the presence of the peptide indicates that the compound is an antagonist to the peptide. The peptide can be labeled, such as by radioactivity.

Other assays and libraries are encompassed within the invention, such as the use of Phylomers® and reverse yeast two-hybrid assays (see Watt, 2006, Nature Biotechnology, 24:177; Watt, U.S. Pat. No. 6,994,982; Watt, U.S. Pat. Pub. No. 2005/0287580; Watt, U.S. Pat. No. 6,510,495; Barr et al., 2004, J. Biol. Chem., 279:41:43178-43189; the contents of each of these publications is hereby incorporated by reference herein in their entirety). Phylomers® are derived from sub domains of natural proteins, which makes them potentially more stable than conventional short random peptides. Phylomers® are sourced from biological genomes that are not human in origin. This feature significantly enhances the potency associated with Phylomers® against human protein targets. Phylogica's current Phylomer® library has a complexity of 50 million clones, which is comparable with the numerical complexity of random peptide or antibody Fab fragment libraries. An Interacting Peptide Library, consisting of 63 million peptides fused to the B42 activation domain, can be used to isolate peptides capable of binding to a target protein in a forward yeast two hybrid screen. The second is a Blocking Peptide Library made up of over 2 million peptides that can be used to screen for peptides capable of disrupting a specific protein interaction using the reverse two-hybrid system.

The Phylomer® library consists of protein fragments, which have been sourced from a diverse range of bacterial genomes. The libraries are highly enriched for stable sub-domains (15-50 amino acids long). This technology can be integrated with high throughput screening techniques such as phage display and reverse yeast two-hybrid traps.

The present application discloses compositions and methods for inhibiting the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides.

The present invention also encompasses pharmaceutical and therapeutic compositions comprising the compounds of the present invention.

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

The present invention is also directed to pharmaceutical compositions comprising the peptides of the present invention. More particularly, such compounds can be formulated as pharmaceutical compositions using standard pharmaceutically acceptable carriers, fillers, solublizing agents and stabilizers known to those skilled in the art.

The invention encompasses the preparation and use of pharmaceutical compositions comprising a compound useful for treatment of the conditions, disorders, and diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

In addition to the active ingredient, a pharmaceutical composition of the invention may further comprise one or more additional pharmaceutically active agents. Particularly contemplated additional agents include anti-emetics and scavengers such as cyanide and cyanate scavengers.

In one embodiment a kit is provided, comprising a compound of the present disclosure and an instructional material which describes administering the composition to a cell or a tissue of a subject. In another embodiment, this kit comprises a (preferably sterile) solvent suitable for dissolving or suspending the composition of the invention prior to administering the compound to the subject. In one embodiment a kit is provided for conducting the method disclosed herein for identifying a regulator of the target molecule of the invention.

The individual amino acid residues of the present (poly) peptides of the invention can be incorporated in the peptide by a peptide bond or peptide bond mimetic. A peptide bond mimetic of the invention includes peptide backbone modifications well known to those skilled in the art. Such modifications include modifications of the amide nitrogen, the alpha carbon, amide carbonyl, complete replacement of the amide bond, extensions, deletions, or backbone cross-links. See, generally, Spatola, Chemistry and Biochemistry of Amino Acids, Peptides and Proteins, Vol. VII (Weinstein ed., 1983). Several peptide backbone modifications are known and can be used in the practice of the invention.

Amino acid mimetics may also be incorporated in the polypeptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to elicit an immune response against the native FtsX T cell epitopes. Amino acid mimetics may include non-protein amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) Ann. Repts. Med. Chem. 24:243-252.

Example 1

Chemokines CXCL9, CXCL10, and CXCL11 Antimicrobial Activity

We tested whether human CXCL9, CXCL10, and CXCL11 exhibited antimicrobial activity against *B. anthra*- cis. These Interferon-inducible (ELR−) CXC chemokines exhibited not only antimicrobial activity against the vegetative form of the organism, but also the spore form such that spore germination was blocked or reduced. An effect on spores is unprecedented, even for any of the traditional antibiotics. We found a hierarchy of activity with human CXCL10>CXCL9>CXCL11 in their ability to kill bacilli and block spore germination. We also tested the effects of recombinant murine CXCL9, CXCL10, and CXCL11 and found similar effects but with a different hierarchy of activity: CXCL9>CXCL10>CXCL11 (of note, human CXCL10 and murine CXCL9 exhibit very similar antimicrobial and anti-spore effects at the same concentrations).

Unless otherwise stated, recombinant human Interferon-inducible (ELR−) CXC chemokines were used for the in vitro studies herein. As controls, we used two recombinant human or mouse C—C family chemokines (CCL2 and CCL5) that have a similar molecular mass and charge (isoelectric point) as CXCL9, CXCL10, and CXCL11, but had no antimicrobial activity against *B. anthracis* spores or bacilli. The initial concentration of the Interferon-inducible (ELR−) CXC chemokines used in our in vitro studies was 48 ug/ml. The 50% effective concentration (EC50) is 4-6 ug/ml for human CXCL10 or murine CXCL9, based on concentration curves using 0-72 ug/ml of interferon-inducible (ELR−) CXC chemokine.

Immunogold electron microscopy (EM) studies of spores treated with CXCL10 demonstrated that CXCL10 localized internal to (not outside) the protective exosporium layer of the spores. In vegetative cells, CXCL10 localized primarily to the cell membrane. These findings suggest that interaction of these Interferon-inducible (ELR−) CXC chemokines with *B. anthracis* spores and vegetative cells is not simply due to a charge-charge interaction with random distribution at the outer surface of the organisms. Preliminary studies performed with stationary phase vegetative bacilli revealed >10-fold more potent CXCL10 killing effect with an EC50 value of 0.33 µg/ml, compared to our previously reported EC50 value of 4-6 µg/ml for CXCL10 against exponential phase organisms.

These findings suggest that the interaction of these Interferon-inducible (ELR−) CXC chemokines with *B. anthracis* spores and bacilli is not simply due to a charge-charge interaction with random distribution at the outer surface of the organisms.

Example 2

In Vivo Activity of CXCL9, CXCL10, and CXCL11

To test the biological relevance of CXCL9, CXCL10, and CXCL11 in vivo, we initially conducted a study comparing susceptible A/J and resistant C57BL/6 mice inoculated with *B. anthracis* Sterne strain spores that luminesce when undergoing germination. Using an in vivo Imaging System (IVIS), spore germination was monitored over time after intranasal inoculation of spores; little to no spore germination occurred in the lungs of the resistant C57BL/6 mice while highly detectable levels of germination were detected in the lungs of the A/J mice. Measurement of CXCL9, CXCL10, and CXCL11 levels in lung homogenates from these animals revealed that C57BL/6 mice had significantly higher levels of CXCL9 and CXCL10 after spore inoculation than did A/J mice. In vivo neutralization studies to further test the biological significance of these Interferon-inducible (ELR−) CXC chemokines revealed that antibody neutralization of CXCL9, CXCL9/CXCL10, or CXCL9/CXCL10/CXCL11, but not CXCR3, rendered the C57BL/6 mice significantly more susceptible to *B. anthracis* Sterne strain infection than the serum control-treated animals. We obtained similar data using CXCR3 knockout mice as well. These data support that there is a direct antimicrobial effect of these Interferon-inducible (ELR−) CXC chemokines in vivo as well as in vitro. Furthermore, the antimicrobial activity of both human and murine CXCL9, CXCL10, CXCL11 has been established using physiological salt concentrations against *B. anthracis* Sterne strain spores and bacilli.

Our observation that these Interferon-inducible (ELR−) CXC chemokines have antimicrobial activities against spores and bacilli opens up an exciting avenue of research for studying host Interferon-inducible (ELR−) CXC chemokines as direct antimicrobial agents and for developing novel therapeutic strategies using these Interferon-inducible (ELR−) CXC chemokines.

Example 3

Determination that ftsX is the Target for CXCL9, CXCL10, and CXCL11

*Bacillus anthracis* FtsX Sequence Information
Protein accession number: YP_031272.1
297 amino acids:
mkaktlsrhl regvknlsrn gwmtfasysa vtvtlllvgv fltaimnmnh fatkveqdve irvhidpaak eadqkkledd mskiakvesi kysskeeelk rlikslgdsg ktfelfeqdnplknvfvvka keptdtatia kkiekmqfvs nvqygkgqve rlfdtvktgr nigivliagllftamflisn tikitiyars teieim-klvg atnwfirwpf lleglflgvl gsiipiglil vtynslqgmf neklggtife llpyspfvfq lagllvliga ligmwgsvms irrflkv (SEQ ID NO: 10)

NCBI Reference Sequence—NC_005945.1; *Bacillus anthracis* str. Sterne, complete genome; >gi|49183039: c4906725-4905832 *Bacillus anthracis* str. Sterne, complete genome:

```
                                           (SEQ ID NO: 11)
ATGAAGGCTAAGACCCTTAGTCGACATTTGCGAGAAGGTGTGAAAA

ATCTATCCCGTAACGGATGGATGACGTTTGCTTCTGTTAGTGCAGT

AACAGTTACACTATTACTTGTAGGTGTCTTTTTAACAGCGATTATG

AATATGAACCATTTTGCGACGAAAGTAGAGCAAGATGTTGAGATTC

GTGTACACATTGATCCAGCAGCAAAAGAAGCTGATCAAAAGAAATT

AGAAGATGATATGAGTAAGATTGCAAAAGTAGAATCTATTAAATAT

TCTTCTAAAGAAGAAGAGTTAAAACGTTTAATTAAAAGCTTAGGCG

ATAGCGGAAAGACGTTTGAGTTATTTGAACAAGATAACCCACTGAA

AAACGTGTTCGTTGTAAAAGCGAAAGAACCAACAGATACAGCAACA

ATTGCGAAAAGATTGAAAAAATGCAGTTTGTAAGTAATGTTCAGT

ACGGAAAAGGGCAAGTTGAACGATTATTTGATACTGTAAAAACTGG

TCGTAACATTGGTATTGTGTTAATTGCTGGTCTTTTATTCACAGCG

ATGTTCTTAATCTCTAACACAATTAAAATTACAATTTATGCTCGTA

GTACAGAAATCGAAATTATGAAACTTGTAGGTGCAACAAACTGGTT

TATTCGTTGGCCGTTCTTGTTAGAGGGATTATTCCTAGGAGTATTA

GGATCAATTATTCCAATTGGCTTAATTCTTGTTACGTATAATTCAC
```

```
-continued
TACAAGGTATGTTTAACGAAAAACTTGGCGGAACAATTTTCGAACT

TCTACCATATAGTCCGTTCGTATTCCAATTAGCTGGTTTACTAGTA

TTAATTGGGGCTTTAATCGGTATGTGGGGAAGCGTAATGTCAATTC

GTCGTTTCTTAAAAGTATAA
```

The Interferon-inducible (ELR−) CXC chemokines, CXCL9, CXCL10 and CXCL11, are important components of host defense in a variety of infections. We now have evidence that interferon-inducible (ELR−) CXC chemokines have direct in vitro antimicrobial activity against B. anthracis spores and bacilli. Furthermore, a putative target of CXCL10 has recently been identified.

1) Human (h) and murine (m) CXCL9, CXCL10, CXCL11 have direct antimicrobial activity at physiological salt concentrations against B. anthracis Sterne strain spores and bacilli in vitro, albeit with different hierarchies of activity: hCXCL10>hCXCL9>hCXCL11 versus mCXCL9>mCXCL10>mCXCL11 (notably, hCXCL10 and mCXCL9 have equivalent in vitro antimicrobial effects).

2) By immunogold EM imaging, CXCL10 localizes to spore structures within and internal to the exosporium, namely, to the spore coat and spore cortex; in vegetative cells, CXCL10 localizes to the cell membrane.

3) CXCL10 exhibits direct antimicrobial activity against spores and encapsulated cells of B. anthracis Ames strain. Under BSL-3 conditions, encapsulated Ames bacilli were incubated with buffer alone or CXCL10 (48 µg/ml) for 6 hr. Aliquots of samples were then plated onto BHI plates. CFU determination was performed after overnight incubation. The presence of capsule was verified for each starting sample using India ink stain and visualization under light microscopy. Encapsulated Ames bacilli incubated with human interferon-inducible (ELR−) CXC chemokines CXCL9 and CXCL11 (48 µg/ml) for 6 hr human were found to also have activity as anti-microbial agents relative to non-interferon-inducible (ELR−) CXC chemokines. Susceptibility to murine interferon-inducible (ELR−) CXC chemokines (48 ug/ml for 6 hr) was tested using an Alamar Blue assay. Murine CXCL9 was more effective than murine CXCL10 which was more effective than CXCL11. These data indicate that the CXC chemokines have antimicrobial effects against both unencapsulated and encapsulated strains of B. anthracis and support the use of Sterne strain as a model organism for the proposed studies.

4) Initial screen of a B. anthracis Sterne strain transposon mutagenesis library using CXCL10 yielded a number of resistant bacterial isolates that are clones—the disrupted gene is annotated as ftsX and encodes the permease component of a prokaryotic ABC transporter.

Identification of a Putative Bacterial Target of CXCL10.

We used an innovative genetic approach to identify a chemokine target in B. anthracis bacilli. This approach entailed use of a mariner-based transposon mutagenesis library adapted for B. anthracis Sterne strain from Listeria monocytogenes and developed by investigators at University of California, Berkeley (Zemansky, (2009) J. Bacteriol. 191:3950-3964). The transposon randomly inserts into the chromosomal and plasmid DNA and is designed to allow sequencing of regions flanking the transposon insertion, thus enabling rapid identification of the disrupted gene. We screened the B. anthracis transposon mutagenesis library for mutants that were resistant (or less susceptible) to CXCL10 and identified eighteen bacterial isolates (TNX1-18) resistant to CXCL10 in two independent screens; 10 of these 18 isolates were confirmed to be resistant to CXCL10 using an Alamar Blue viability assay. In multiple isolates, the disrupted gene was identified by PCR and DNA sequencing as BAS5033, annotated as ftsX. This gene has a high degree of homology to the gene that encodes the Bacillus subtilis FtsX, an integral membrane protein component of an ABC transporter that functions by importing signals involved in the initiation of sporulation. This finding raises intriguing questions about whether the B. anthracis homologue of FtsX plays a role in transporting components/nutrients related to the maintenance of viability and is a direct (or indirect) target of CXCL10, or alternatively is involved in the uptake of CXCL10 into the organism.

We successfully created a knockout mutant of ftsX by bacteriophage transduction (designated as the "ftsX mutant") using published protocols and confirmed resistance of this mutant to CXCL10. The B. anthracis ftsX mutant strain is resistant to CXCL10 (48 ug/ml for 6 hr) based on an Alamar Blue assay. Strains tested were: the transposon mutagenesis library, TNX18 isolated from the screen, and the ftsX mutant. Both TNX18 and the ftsX mutant strain exhibited resistance to CXCL10.

Furthermore, we have found that this mutant strain is also resistant to CXCL9 and CXCL11, which supports our hypothesis that CXCL9, CXCL10, and CXCL11 have a common target in vegetative bacteria. Specifically, susceptibilities to human CXCL9 and CXCL11 (48 ug/ml for 6 hr each) were tested using an Alamar Blue assay. Strains tested were: B. anthracis parent strain, transposon mutagenesis library, TNX18, and the ftsX mutant. TNX18 and the ftsX mutant were resistant to CXCL9. All strains were resistant to CXCL11, which is consistent with the less effective antimicrobial activity observed for human CXCL11.

Site-Directed Mutagenesis Studies.

Without wishing to be bound by any particular theory, we hypothesize that CXCL10 (as well as CXCL9 and CXCL11) interacts with the predicted extracellular portions of FtsX. To assess which portions of FtsX may interact with CXCL10, we will use allelic exchange to create deletion mutants of segments of the extracellular portions of FtsX. If deletion of a segment of FtsX abrogates the CXCL10 effect on the bacilli, we will narrow our studies to focus on key amino acids responsible for the interaction and/or effect of CXCL10; to do this, we will perform site-directed mutagenesis with substitution of neutral amino acids (alanine) for select amino acids in the portion of FtsX that may be responsible for the interaction or effect of CXCL10. We will initially target negatively charged amino acids that are clustered together since the net charge distribution is likely to play an important role in the interaction with CXCL10, which has a positively charged carboxyl terminus. The ability of the site-directed mutagenesis to disrupt interactions between the interferon-inducible (ELR−) CXC chemokine and FtsX will be assessed by in vitro susceptibility testing of the mutant bacterial strain to the interferon-inducible (ELR−) CXC chemokine. Further, using a GFP-tagged version of FtsX, we will perform: 1) co-localization studies with immunofluorescence microscopy; and 2) immunoprecipitation coupled with Western blot analyses to determine if the mutated FtsX can be co-precipitated with antibodies to the specific interferon-inducible (ELR−) CXC chemokine.

Expected Results and Interpretations.

We expect that FtsX is the target for CXCL9, CXCL10, and CXCL11. Furthermore, we anticipate that the interaction between chemokine and FtsX is a direct interaction at the extracellular portion of the permease at a location where there is a net negative charge distribution. We anticipate that co-localization immunofluorescence experiments will reveal that the proteins interact at the cell membrane. Further, we predict that performing site-directed mutagenesis of select extracellular portions and then select (negatively charged) amino acids will abrogate the interaction and the antimicrobial effect of the interferon-inducible (ELR−) CXC chemokine against the bacilli.

Potential Pitfalls and Alternative Approaches.

It is possible that the interaction is indirect and CXCL10 interacts with another molecule upstream of the permease. For example, an indirect target might be the substrate binding protein (SBP) that is typically associated with these ABC transporters. We have identified a gene present in the B. anthracis genome that has sequence homology with ftsY, a SBP gene found in other organisms such as B. subtilis and E. coli. Thus, one alternative approach will be to delete this putative SBP gene and test the susceptibility of a ΔftsY mutant strain to CXCL10 and compare the results to those obtained using the ΔftsX strain.

Example 4

Utilizing the interferon-inducible interferon-inducible (ELR−) CXC chemokines to elicit a protective effect in vivo against pulmonary anthrax infection in a mouse model.

The data described herein support the notion that the interferon-inducible interferon-inducible (ELR−) CXC chemokines play a direct and critical role in protecting the host against pulmonary anthrax. In addition to the in vitro data already presented in Examples 1-3, in vivo data provide further support as follows:

1) CXCL9, CXCL10, CXCL11 are markedly induced and expressed early in the lungs of C57BL/6 mice, which are highly resistant to inhalational spore challenge.

2) CXCL10−/− mice have significantly higher numbers (CFUs) of B. anthracis spores and vegetative bacilli after spore challenge than do the wild type parent C57BL/6 mice.

Figure 2:
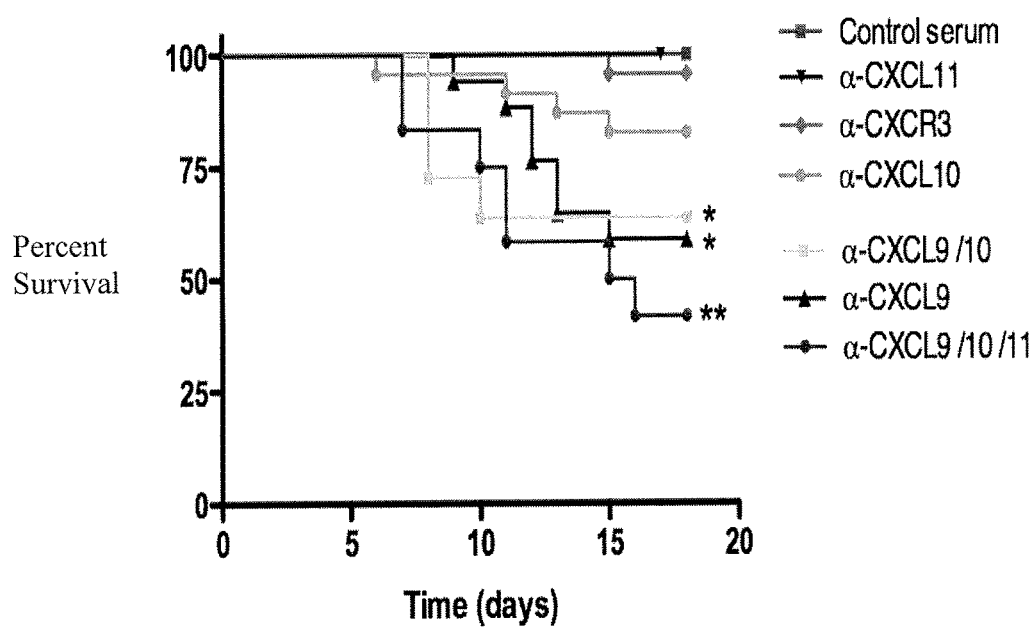
FIG. 2 Neutralization of CXCL9, CXCL9/CXCL10, or CXCL9/10/11 but not CXCR3 renders C57BL/6 mice susceptible to *B. anthracis* infection. C57BL/6 mice received injections of anti-CXCL9, CXCL10, and/or CXCL11 antibodies or anti-CXCR3 antibodies or control goat serum, as indicated in the figure, one day prior to intranasal inoculation with *B. anthracis* Sterne strain spores and then daily throughout the experiment. Mice were monitored for survival over an 18-day period. *p-value<0.05; **p-value<0.01 compared to spore-inoculated animals that received control goat serum.

3) Ab neutralization of CXCL9, CXCL9/CXCL10, CXCL9/CXCL10/CXCL11 significantly increased the susceptibility of C57BL/6 mice to anthrax infection but neutralization of the chemokine receptor (CXCR3) had no significant effect on C57BL/6 susceptibility to inhalational anthrax (FIG. 2).

Neutralization of CXCL9, CXCL9/CXCL10, or CXCL9/CXCL10/CXCL11 but not CXCR3 renders C57BL/6 mice susceptible to B. anthracis spore challenge. To assess the biological role of CXCL9, CXCL10, CXCL11, or their shared CXCR3 receptor (which is expressed by leukocytes recruited by CXCL9-11), we performed a survival study using C57BL/6 mice that received intraperitoneal (i.p.) injections of control serum or anti-CXCL9, anti-CXCL10, anti-CXCL11, anti-CXCL9+anti-CXCL10, anti-CXCL9+anti-CXCL10+anti-CXCL11, or anti-CXCR3 serum 24 hr prior to intranasal spore challenge and then daily throughout the experiment, using published protocols. The anti-CXCL9, CXCL10, and CXCL11 neutralizing antibodies have been validated in published work. As shown in FIG. 2, mice that received anti-CXCL9, anti-CXCL9+anti-CXCL10, or anti-CXCL9+anti-CXCL10+anti-CXCL11 had significantly decreased survival after spore challenge. The other groups, including animals that received anti-CXCR3, had no significant difference in survival compared to normal serum controls that received spore challenge. These findings suggest that CXCL9, CXCL10, CXCL11 have significant direct antimicrobial effects against B. anthracis in vivo that may be independent of cell recruitment of CXCR3-expressing cells.

Example 5

Generation of a B. anthracis DftsX Mutant Strain

Figure 3A:
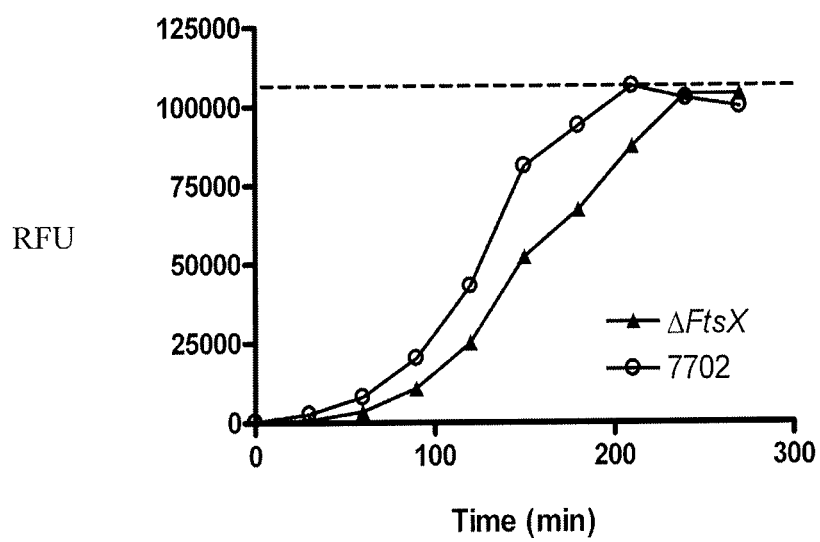
FIGS. 3A & 3B provide a graph showing the growth curve of ΔftsX compared to the parent *B. anthracis* Sterne strain 7702 (FIG. 3A) and resistance of the ΔftsX strain to CXCL10-mediated killing compared to *B. anthracis* Sterne strain 7702 (FIG. 3B; designated "7702 wt" in graph). Growth curves were generated using an Alamar Blue assay; RFU=relative fluorescence units. Susceptibility to CXCL10 was determined by a 1 hr incubation with 0-24 ug/ml CXCL10; viability was determined using an Alamar Blue assay; n=3-5 expts.
Figure 3B:
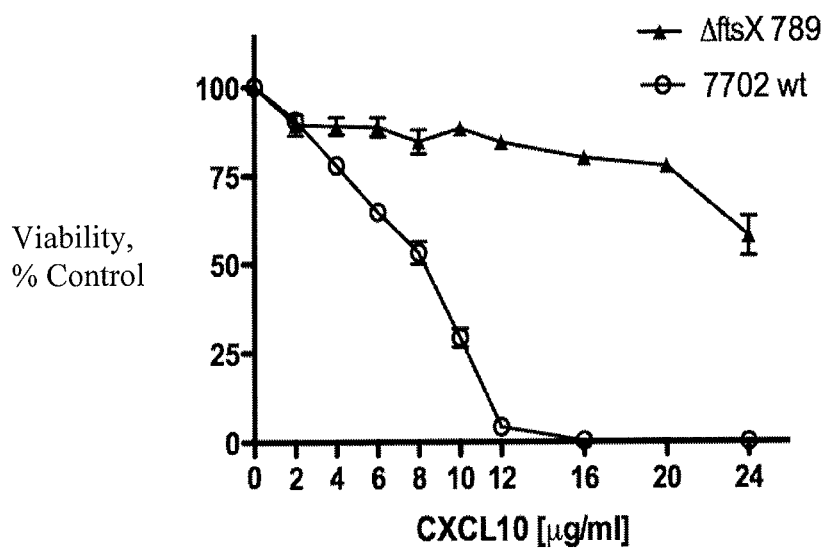

Markerless allelic exchange was used to create a deletion mutant of the ftsX gene in wild type B. anthracis Sterne strain (designated "ΔftsX"). Growth characteristics are shown in FIG. 3A for B. anthracis Sterne strain 7702 and ΔftsXΔftsX. The ΔftsX strain grows more slowly than wild type strain. The ΔftsX strain has a distinctive phenotype such that bacilli grow in "kinked" chains due to various angles produced at septations between individual bacilli. Sporulation occurs with ΔftsX but with a lower yield than that of the parent strain. We confirmed resistance of ΔftsX to CXCL10 (FIG. 3B). Furthermore, we found that ΔftsX was also resistant to CXCL9 and CXCL11, which supports that CXCL9, CXCL10, and CXCL11 have a common target in vegetative bacteria. Additionally, in contrast to B. anthracis Sterne 7702 strain, the ΔftsX exponential and stationary phase organisms are both resistant to CXCL10.

Example 6

Identification of Escherichia coli Pyruvate Dehydrogenase Complex as an Important Component of CXCL10-Mediated Antimicrobial Activity Materials and Methods:
Bacterial Strains and Growth Conditions:

E. coli parent strain (BW25113) and its derivatives ΔaceE, ΔaceF and ΔlpdA (JW0110-2, JW0111-2 and JW0112-3) were obtained from the Keio Collection (22) via the Coli Genetic Stock Center, and were used in all experiments. E. coli strain Alpha-select (Bioline) was used for propagation of aceE-containing and empty cloning vector pBR322.

Transposon Library Generation, Screening of Mutant Library, and Determination of Insertion Site:

EZ-Tn5™<KAN-2>Tnp Transposome™ Kit (Catalog #TSM99K2, Epicentre® Biotechnologies, Madison, Wis.) was used to generate a transposon library in E. coli parent strain according to the manufacturer's instructions. E. coli genes were randomly interrupted by insertion of EZ-Tn5 Transposase recognition sequences surrounding a kanamycin resistance gene, Tn903. Bacilli were prepared from a pooled E. coli transposon library and treated with 36 and 48 μg/mL recombinant human CXCL10 or vehicle alone (untreated) for 2 h at 37° C., after which time dilutional aliquots were plated on LB agar for determination of colony forming units (cfu)/mL. Fifteen viable transposon mutants were identified from this primary screen, designated as Tnx1-Tnx15. Resistant transposon mutants then underwent secondary screening with either 6 μg/mL CXCL10 or the vehicle alone to determine their level of CXCL10 resistance as compared to the E. coli parent strain. Transposon insertion sites in the two CXCL10 resistant transposon mutants were determined by PCR. After linker ligation, PCR enrichment of single-stranded DNA fragments flanking the transposon insertion site was performed, with subsequent purification and excision from agarose gel with the QIAquick gel extraction kit (Catalog #28704, Qiagen®, Germantown, Md.). PCR with Y-linker primer and either Kan-2-FP-1 or Kan-2-RP-1 followed by purification and excision from agarose gel yielded the PCR product submitted for sequencing.

Antimicrobial Assays:

E. coli strains were treated with recombinant human CXCL10 (Catalog #300-12, PeproTech®, Rocky Hill, N.J.) in 10 mM potassium phosphate buffer (pH 7.4) supplemented with 1% tryptic soy broth.

Gene Complementation:

The E. coli parent strain aceE gene along with its native promoter and ribosomal binding site were inserted into plasmid pBR322. Plasmid vectors were subsequently transformed into electro-competent E. coli parent and ΔaceE strain bacteria.

Examination of Bacterial Growth Rates:

Standard methodology was used to determine bacterial growth rates.

Silver-Enhanced Immunogold Labeling and Visualization with Transmission EM:

A modified pre-embedding protocol was used to perform CXCL10 immunogold labeling with silver enhancement (Belperio J. A. et al., 2002. J. Clin. Invest. 110:1703-1716. [PMCID: PMC151632]).

Statistical Analysis:

GraphPad Prism software (version 4.0 or 6.0) was used for statistical analysis and graphing. P values<0.05 were considered statistically significant.

Results:

Generation and screening of a transposon mutant library to detect E. coli isolates resistant to CXCL10-mediated antibacterial effects We constructed a transposon mutant library from E. coli K12 BW25113 (henceforth referred to as the parent strain). The resultant pooled library of transposon mutants was subsequently screened for resistance to CXCL10 by exposure to 36 μg/mL (4.2 μM) and 48 μg/mL (5.6 μM) of the chemokine, concentrations at which the parent strain is killed. Fifteen transposon mutants, designated Tnx1-Tnx15, were isolated from this primary screen.

Figure 4:
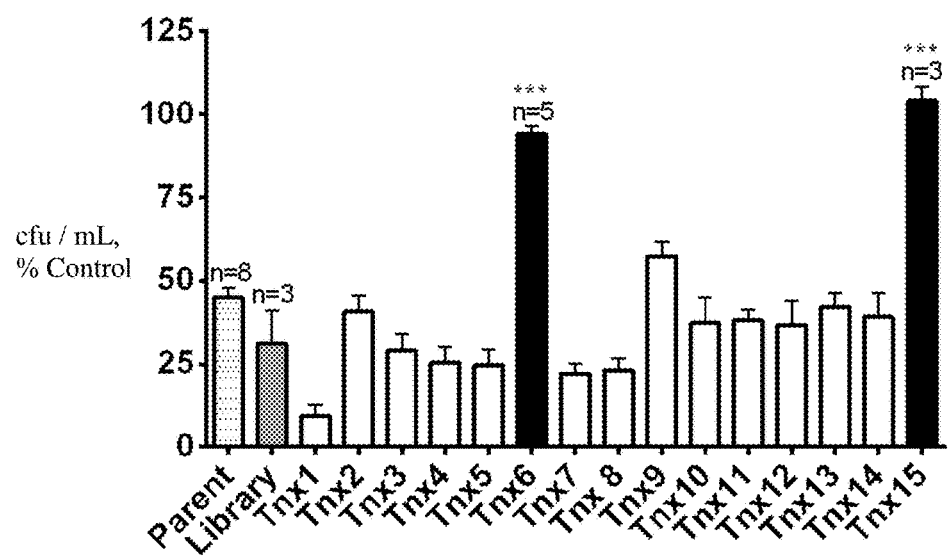
FIG. 4 Secondary susceptibility screen of mutants isolated from *E. coli* transposon mutant library treated with CXCL10. A pooled *E. coli* transposon library of bacterial mutants was initially treated with 3% human serum albumin (HSA) alone (untreated) or 36 and 48 μg/mL recombinant human CXCL10 in 3% HSA. Fifteen viable transposon mutants were isolated and designated as Tnx1-Tnx15. In a secondary screen of bacterial isolate resistance, transposon mutants Tnx1-Tnx15 were individually examined for their level of CXCL10 resistance as compared to the *E. coli* parent strain. Bacteria were treated with 6 μg/mL CXCL10 or the 3% HSA vehicle alone for 2 h and then dilutional aliquots were plated on LB agar and incubated overnight at 37° C. to determine colony forming units (cfu)/mL. Data are expressed as a percentage of the isolate-specific untreated control and represent mean values±SEs of the means (SEM); n=2 independent experiments except where otherwise noted. ***P<0.0001 compared with CXCL10-treated parent strain bacteria (checkered bar); isolates represented by open bars were not significantly resistant to CXCL10.

Following the primary screen of the transposon mutant library, a secondary screen was performed in which the 15 previously identified CXCL10 resistant transposon mutants (designated Tnx1-Tnx15) were isolated and individually tested for susceptibility to CXCL10. In the secondary screen, each isolate was exposed to a lower concentration of chemokine (6 μg/mL). Since the parent strain is not entirely killed by this CXCL10 concentration, secondary screening with a lower concentration of CXCL10 allowed for comparison of the relative level of susceptibility to CXCL10 between each of the selected transposon mutants and the parent strain (FIG. 4). Two transposon mutants, Tnx 6 and Tnx 15, exhibited significantly decreased susceptibility to CXCL10 in relation to the parent strain.

Identification of aceE Gene Disruption in CXCL10 Resistant Tnx Isolates

Through genetic sequencing, the transposon insertion site was determined and the interrupted gene was identified. Using previously described methods adapted for use with EZ-Tn5TM<KAN-2>Tnp Transposome™, we isolated and digested chromosomal DNA from Tnx 6 and Tnx 15, then ligated the DNA digests with a partially double stranded Y-linker. The ligation product was purified, after which initial PCR enrichment for single-stranded DNA segments flanking the transposon insertion was performed using Epicentre Kan-2-FP-1 and Kan-2-RP-1 primers. Two unique insertion sites were identified, both of which resulted in the disruption of a single gene, aceE, which encodes the E1 subunit of the E. coli PDHc.

Pyruvate dehydrogenase is a large enzyme complex, consisting of multimers of each of its three subunits, E1p, E2p, and E3p, which are encoded by the genes aceE, aceF and lpdA, respectively. The ratio of subunit types, and the corresponding enzyme complex structure, differs between Gram-negative and Gram-positive bacteria, with the complex in the latter more closely resembling PDHc found in eukaryotic cells. Through catalyzing the conversion of pyruvate to acetyl coenzyme A (acetyl-CoA), PDHc serves as an important link between glycolysis and the TCA cycle, both of which function in aerobic respiration. Products of the TCA cycle such as nicotinamide adenine dinucleotide (NAD) supply electrons for use within the electron transport chain, providing proton motive force and establishing an electrochemical gradient across the bacterial membrane that is used to replenish bacterial energy in the form of adenosine triphosphate (ATP). In addition to its central role within the TCA cycle, acetyl-CoA is also a required substrate for the first committed step in fatty acid synthesis, the conversion of acetyl-CoA to malonyl-CoA by acetyl-CoA carboxylase.

Testing of ΔaceE and Other E. coli Susceptibility to CXCL10

Figure 5:
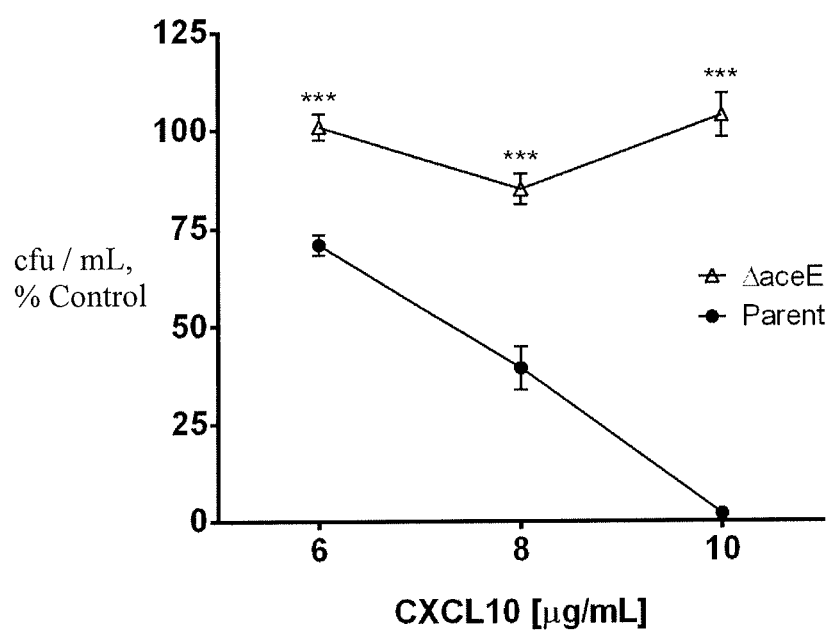
FIG. 5 An *E. coli* aceE deletion mutant strain (ΔaceE) exhibits resistance to CXCL10-mediated antimicrobial activity. *E. coli* parent strain and ΔaceE were treated with CXCL10 for 2 h and then dilutional aliquots were plated on LB agar for cfu/mL determination after overnight incubation at 37° C. Reduction in bacterial viability is expressed as a percentage of untreated (vehicle alone) control for each strain. Data points represent mean values±SEM; n=3 independent experiments with 4 replicates, *** P<0.0001.

To further explore the role of aceE in the susceptibility of E. coli to CXCL10, an E. coli BW25113-derived aceE deletion mutant (JW0110-2) was obtained from the Keio Collection via the Coli Genetic Stock Center. Susceptibility of this ΔaceE strain was compared to that of the E. coli parent strain at increasing concentrations of CXCL10 (FIG. 5). E. coli parent strain was killed after exposure to 10 μg/mL CXCL10 for 2 hours, while ΔaceE, similar to Tnx6 and Tnx15, was significantly less susceptible to CXCL10-mediated antimicrobial effect.

Figure 6:
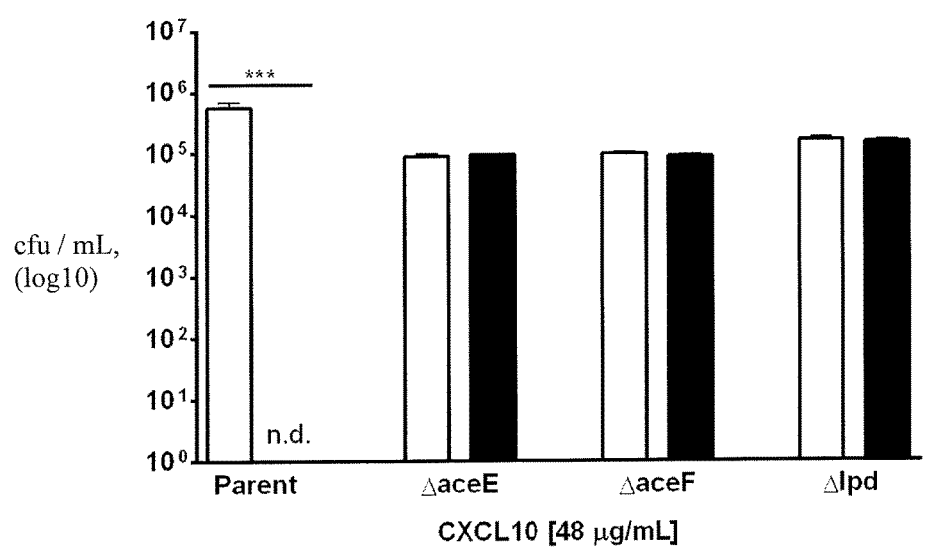
FIG. 6 CXCL10-mediated antimicrobial activity against *E. coli* parent strain and pyruvate dehydrogenase complex (PDHc) subunit deletion mutants (ΔaceE, ΔaceF, and ΔlpdA). *E. coli* parent strain and PDHc subunit deletion mutants, ΔaceE, ΔaceF and ΔlpdA, were treated with 48 μg/mL CXCL10 or vehicle alone (untreated) for 2 h, after which samples were plated on LB agar to determine cfu/mL following overnight incubation at 37° C. Average initial inoculums were $1.7 \times 10^5$ for the parent strain, $1.9 \times 10^5$ for ΔaceE, $2.4 \times 10^5$ for ΔaceF and $3.9 \times 10^5$ for ΔlpdA. Data are expressed as log 10 cfu/mL, with open bars for untreated control and black bars for CXCL10-treated groups; bars represent mean values±SEM; n=3 independent experiments with 3 replicates, ***P<0.0001, n.d.=not detected, <50 cfu/mL.

To determine whether this killing effect was dependent upon the presence of the aceE gene product E1p alone, or its functional end product PDHc, additional Keio collection deletion mutant strains were obtained lacking either aceF or lpdA (Keio strain designation JW0111-2 and JW0112-3), which encode the remaining subunits of PDHc (E2p and E3p, respectively). All three deletion mutant strains were found to be equally resistant to the antimicrobial effects of CXCL10, even after exposure to chemokine concentrations as high as 48 μg/mL (FIG. 6). Together these data suggest that the disruption of functional PDHc rather than of aceE and the resultant enzyme it encodes, confers decreased susceptibility to the antimicrobial effect of CXCL10.

Restoration of the Parent Strain E. coli CXCL10 Susceptibility Phenotype in ΔaceE The correlation between disruption of aceE and the observed decrease in CXCL10 susceptibility was tested through aceE complementation studies. The E. coli parent strain aceE gene along with its promoter and ribosomal binding site were amplified, double digested, purified and then ligated into the plasmid vector pBR322. The plasmid vector containing the aceE insert or an empty vector (as a control) was individually transformed into Alpha-select E. coli (Bioline) for propagation and then isolated. Gene sequencing was performed to verify the appropriate insertion of aceE into pBR322. Each plasmid vector was subsequently transformed into electro-competent E. coli parent strain and ΔaceE bacteria. These complemented transformants were validated by diagnostic PCR and gene sequencing.

Figure 7:
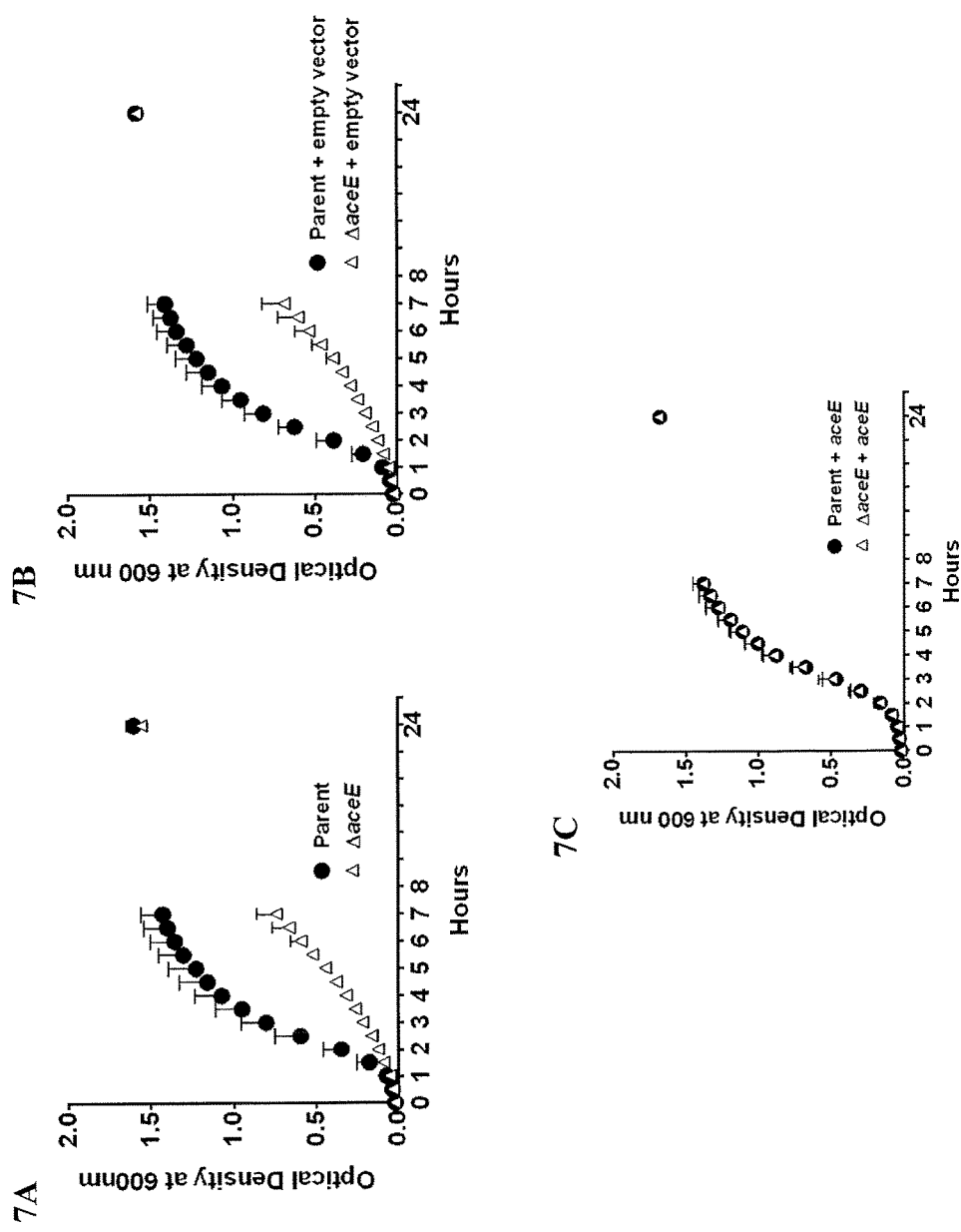
FIGS. 7A-7C. Complementation of *E. coli* ΔaceE with the aceE gene restores an *E. coli* parent strain growth phenotype.
Figure 8:
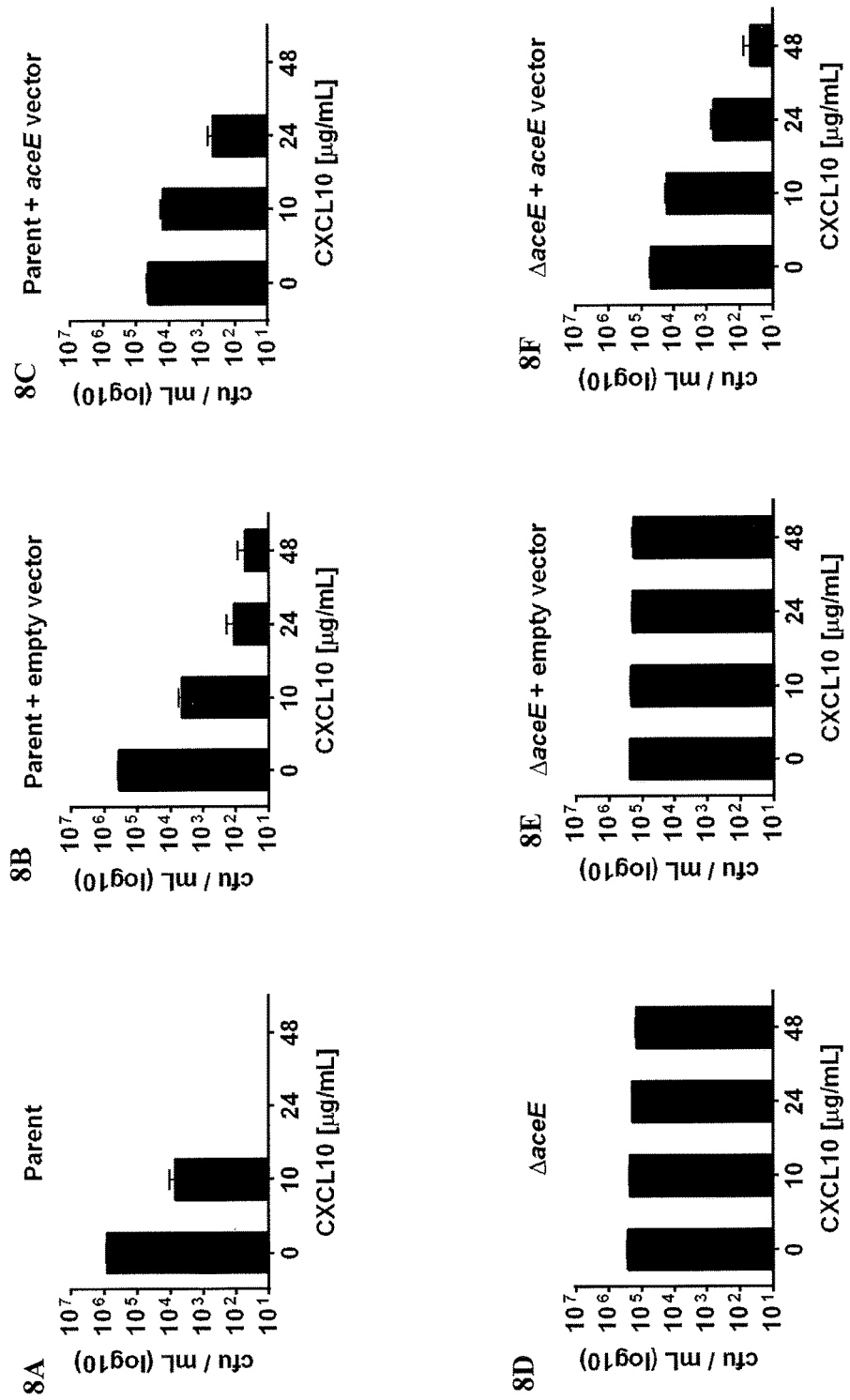
FIGS. 8A-8F. Complementation of *E. coli* ΔaceE with the aceE gene restores the parent strain CXCL10 susceptibility phenotype.

Comparison of the growth curves of E. coli parent strain and ΔaceE revealed that ΔaceE exhibited a slower growth rate (FIG. 7A). The observed difference in growth rate between parent strain and ΔaceE was retained following complementation of each strain with empty vector only (FIG. 7B). In contrast, when the ΔaceE strain was complemented with aceE, its growth curve phenotype was restored to that of the parent strain (FIG. 7C). Similarly, complementation of E. coli ΔaceE with aceE restored susceptibility to CXCL10 to a level equivalent to the parent stain, whereas there was no change in susceptibility phenotype of either the parent or aceE deletion mutant strain when complemented with empty vector, or in the E. coli parent strain when complemented with aceE (FIG. 8).

Localization of CXCL10 to the Bacterial Cell Surface of Both E. coli Parent Strain and ΔaceE Silver-enhanced immunogold labeling of CXCL10 was performed to determine chemokine localization following incubation with either E. coli parent strain or ΔaceE bacteria. Bacteria were exposed to CXCL10 at a concentration of 48 µg/mL for 30 minutes. CXCL10 localization was then determined using silver-enhanced immunogold labeling of CXCL10 and visualized by transmission EM. CXCL10-treated ΔaceE bacteria demonstrated localization of CXCL10 to the bacterial membrane, similar to CXCL10-treated parent strain bacteria. PDHc is thought to reside within the bacterial cytosol; however, immunogold labeled CXCL10 was not identified within the cytosol of either strain of E. coli under the conditions tested. Instead, in both the parent strain and ΔaceE, electron microscopy studies revealed localization of CXCL10 to the bacterial cell surface. These data indicate that CXCL10 interacts with a bacterial surface component rather than directly with the PDHc.

Discussion:

This study establishes the importance of specific bacterial components in the in vitro CXCL10-mediated killing of E. coli. Through generation and screening of an E. coli transposon mutant library, we isolated two transposon mutants with significantly decreased susceptibility to CXCL10-mediated antimicrobial effects. Both mutants contained unique disruptions within the gene aceE, which encodes E1p, the E1 subunit of PDHc. PDHc consists of multimers of three distinct subunits, E1p, E2p and E3p, all of which are required for its activity as a functional enzyme. Disruption of PDHc by deletion of any of the genes encoding one of its three subunits resulted in similar decreases in susceptibility to CXCL10-mediated antimicrobial activity. Both the growth phenotype and susceptibility to CXCL10 were restored in E. coli ΔaceE after complementation with a plasmid vector carrying the aceE gene.

Although PDHc is located in the bacterial cytosol, immunogold electron microscopy studies to evaluate localization of CXCL10 revealed that the chemokine appears to localize to the bacterial surface in both E. coli parent strain and ΔaceE. One possible explanation for these findings is that CXCL10 interacts with a common moiety present on the surface of both E. coli parent strain and ΔaceE, and that this interaction results in downstream antimicrobial effects dependent upon the presence of functional PDHc. In the event that additional, essential bacterial cell surface, membrane, or periplasmic targets exist, mutations to the genes encoding such components may be lethal, preventing their detection during screening of our transposon mutant library. Under aerobic conditions such as those used in our experiments, PDHc provides the primary means for production of acetyl-CoA, which serves as a central component for many different metabolic processes including the TCA cycle, the glyoxylate shunt, glycolysis, gluconeogenesis, and fatty acid synthesis. Two additional pathways for the production of acetyl-CoA have been described, but the first, which utilizes the enzyme pyruvate formate-lyase (PFL), functions mostly under anaerobic conditions. The second pathway uses the enzyme pyruvate oxidase (PoxB) to convert pyruvate to acetate, which is then irreversibly converted to acetyl-CoA in vivo by adenosine monophosphate-forming acetyl-CoA synthase (AMP-ACS). This second pathway is normally used by E. coli to produce acetyl-CoA during stationary phase or under microaerobic conditions, although when over-expressed or constitutively expressed it has the ability to function as a less efficient substitute for PDHc. It is possible that E. coli ΔaceE bacteria are somehow able to avoid CXCL10-mediated killing by directing energy production away from aerobic respiration and the TCA cycle, and instead forcing it to proceed through other, less efficient metabolic pathways. Interestingly, although all three of the genes encoding PDHc subunits are essential in E. coli when glucose is the only available source of carbon, none are essential when bacteria are grown on Luria-Bertani (LB) media.

What is claimed is:

1. A method for identifying antimicrobial agents, said method comprising
    contacting a parent *E coli* strain and a derivative strain with a candidate compound, wherein the derivative strain has been modified relative to said parent strain to be deficient in pyruvate dehydrogenase complex (PDHC) function further wherein said candidate compound is not an aminoglycoside;
    culturing the parent *E coli* strain and said derivative strain under conditions suitable for growth;
    identifying those candidate compounds that inhibit the growth of parent *E. coli* strain relative to the PDHC-deficient *E. coli* derivatives as antimicrobial agents.

2. The method of claim 1 wherein the identified antimicrobial agent is one that inhibits the parent *E. coli* growth 2-fold greater than said PDHC-deficient *E. coli* derivative.

3. The method of claim 2 wherein the PDHC-deficient *E. coli* derivative is a pyruvate dehydrogenase complex subunit deletion mutant selected from the group consisting of ΔaceE, ΔaceF, and ΔlpdA.

4. The method of claim 3 wherein the pyruvate dehydrogenase complex subunit deletion mutant is ΔaceE.

5. A method for identifying antimicrobial agents, said method comprising
    i) screening candidate compounds to identify compounds that bind to the *B. anthracis* FtsE/X complex;
    ii) contacting a parent *E coli* strain and a derivative strain with a candidate compound identified in step i), wherein the derivative strain has been modified relative to said parent strain to be deficient in pyruvate dehydrogenase complex (PDHC) function;
    iii) culturing the parent *E coli* strain and said derivative strain under conditions suitable for growth;
    iv) selecting those candidate compounds identified in step i) that inhibit the growth of parent *E. coli* strain relative to the PDHC-deficient *E. coli* derivatives as antimicrobial agents.

6. A method for identifying antimicrobial agents, said method comprising
    i) screening candidate compounds to identify compounds that bind to the peptide KVEQDVEIRVHID-PAAKEADQKKLEDD (SEQ ID NO: 18);
    ii) contacting a parent *E coli* strain and a derivative strain with a candidate compound identified in step i), wherein the derivative strain has been modified relative to said parent strain to be deficient in pyruvate dehydrogenase complex (PDHC) function;
    iii) culturing the parent *E coli* strain and said derivative strain under conditions suitable for growth;
    iv) selecting those candidate compounds identified in step i) that inhibit the growth of parent *E. coli* strain relative to the PDHC-deficient *E. coli* derivatives as antimicrobial agents.

7. The method of claim 1 further comprising a step of screening the identified microbial agents for the ability to bind to the *B. anthracis* FtsE/X complex, wherein compounds that bind to bind to the *B. anthracis* FtsE/X complex are selected as a further subset of antimicrobial agents.

8. The method of claim 1 further comprising a step of screening the identified microbial agents for the ability to bind to the peptide (SEQ ID NO: 18)
KVEQDVEIRVHIDPAAKEADQKKLEDD, wherein compounds that bind to SEQ ID NO: 18 are selected as a further subset of antimicrobial agents.

* * * * *

SEQUENCE LISTING

```
<160> NUMBER OF SEQ ID NOS: 18

<210> SEQ ID NO 1
<211> LENGTH: 88
<212> TYPE: PRT
<213> ORGANISM: Homo sapiens

<400> SEQUENCE: 1

Lys Ser Gly Val Leu Phe Leu Leu Gly Ile Ile Leu Leu Val Leu Ile
1               5                   10                  15

Gly Val Gln Gly Thr Pro Val Val Arg Lys Gly Arg Cys Ser Cys Ile
            20                  25                  30

Ser Thr Asn Gln Gly Thr Ile His Leu Gln Ser Leu Lys Asp Leu Lys
        35                  40                  45

Gln Phe Ala Pro Ser Pro Ser Cys Glu Lys Ile Glu Ile Ile Ala Thr
    50                  55                  60

Leu Lys Asn Gly Val Gln Thr Cys Leu Asn Pro Asp Ser Ala Asp Val
```

```
                65                  70                  75                  80
Lys Glu Leu Ile Lys Lys Trp Glu
                        85

<210> SEQ ID NO 2
<211> LENGTH: 88
<212> TYPE: PRT
<213> ORGANISM: Mus musculus

<400> SEQUENCE: 2

Lys Ser Ala Val Leu Phe Leu Leu Gly Ile Ile Phe Leu Glu Gln Cys
1               5                   10                  15

Gly Val Arg Gly Thr Leu Val Ile Arg Asn Ala Arg Cys Ser Cys Ile
            20                  25                  30

Ser Thr Ser Arg Gly Thr Ile His Tyr Lys Ser Leu Lys Asp Leu Lys
        35                  40                  45

Gln Phe Ala Pro Ser Pro Asn Cys Asn Lys Thr Glu Ile Ile Ala Thr
    50                  55                  60

Leu Lys Asn Gly Asp Gln Thr Cys Leu Asp Pro Asp Ser Ala Asn Val
65                  70                  75                  80

Lys Lys Leu Met Lys Glu Trp Glu
                        85

<210> SEQ ID NO 3
<211> LENGTH: 88
<212> TYPE: PRT
<213> ORGANISM: Artificial Sequence
<220> FEATURE:
<223> OTHER INFORMATION: Modified human CXCL9 chemokin
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
```

```
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid

<400> SEQUENCE: 3

Lys Ser Xaa Val Leu Phe Leu Leu Gly Ile Ile Xaa Leu Xaa Xaa Xaa
1               5                   10                  15

Gly Val Xaa Gly Thr Xaa Val Xaa Arg Xaa Xaa Arg Cys Ser Cys Ile
            20                  25                  30

Ser Thr Xaa Xaa Gly Thr Ile His Xaa Xaa Ser Leu Lys Asp Leu Lys
        35                  40                  45

Gln Phe Ala Pro Ser Pro Xaa Cys Xaa Lys Xaa Glu Ile Ile Ala Thr
50                  55                  60

Leu Lys Asn Gly Xaa Gln Thr Cys Leu Xaa Pro Asp Ser Ala Xaa Val
65                  70                  75                  80

Lys Xaa Leu Xaa Lys Xaa Trp Glu
                85

<210> SEQ ID NO 4
<211> LENGTH: 98
<212> TYPE: PRT
<213> ORGANISM: Homo sapiens

<400> SEQUENCE: 4

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro
```

<210> SEQ ID NO 5
<211> LENGTH: 98
<212> TYPE: PRT
<213> ORGANISM: Mus musculus

<400> SEQUENCE: 5

Met Asn Pro Ser Ala Ala Val Ile Phe Cys Leu Ile Leu Leu Gly Leu
1               5                   10                  15

Ser Gly Thr Gln Gly Ile Pro Leu Ala Arg Thr Val Arg Cys Asn Cys
            20                  25                  30

Ile His Ile Asp Asp Gly Pro Val Arg Met Arg Ala Ile Gly Lys Leu
        35                  40                  45

Glu Ile Ile Pro Ala Ser Leu Ser Cys Pro Arg Val Glu Ile Ile Ala
    50                  55                  60

Thr Met Lys Lys Asn Asp Glu Gln Arg Cys Leu Asn Pro Glu Ser Lys
65                  70                  75                  80

Thr Ile Lys Asn Leu Met Lys Ala Phe Ser Gln Lys Arg Ser Lys Arg
                85                  90                  95

Ala Pro

<210> SEQ ID NO 6
<211> LENGTH: 98
<212> TYPE: PRT
<213> ORGANISM: Artificial Sequence
<220> FEATURE:
<223> OTHER INFORMATION: Modified human CXCL10 chemokin
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(38)

```
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (44)..(46)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(92)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid

<400> SEQUENCE: 6

Met Asn Xaa Xaa Ala Xaa Xaa Ile Xaa Cys Leu Ile Xaa Leu Xaa Leu
1               5                   10                  15

Ser Gly Xaa Gln Gly Xaa Pro Leu Xaa Arg Thr Val Arg Cys Xaa Cys
            20                  25                  30

Ile Xaa Ile Xaa Xaa Xaa Pro Val Xaa Xaa Arg Xaa Xaa Xaa Lys Leu
        35                  40                  45

Glu Ile Ile Pro Ala Ser Xaa Xaa Cys Pro Arg Val Glu Ile Ile Ala
    50                  55                  60

Thr Met Lys Lys Xaa Xaa Glu Xaa Arg Cys Leu Asn Pro Glu Ser Lys
65                  70                  75                  80

Xaa Ile Lys Asn Leu Xaa Lys Ala Xaa Ser Xaa Xaa Arg Ser Lys Arg
                85                  90                  95

Xaa Pro

<210> SEQ ID NO 7
<211> LENGTH: 75
<212> TYPE: PRT
<213> ORGANISM: Homo sapiens

<400> SEQUENCE: 7

Gln Gly Phe Pro Met Phe Lys Arg Gly Arg Cys Leu Cys Ile Gly Pro
1               5                   10                  15

Gly Val Lys Ala Val Lys Val Ala Asp Ile Glu Lys Ala Ser Ile Met
            20                  25                  30

Tyr Pro Ser Asn Asn Cys Asp Lys Ile Glu Val Ile Ile Thr Leu Lys
```

-continued

```
                35                  40                  45

Glu Asn Lys Gly Gln Arg Cys Leu Asn Pro Lys Ser Lys Gln Ala Arg
            50                  55                  60

Leu Ile Ile Lys Lys Val Glu Arg Lys Asn Phe
65                  70                  75

<210> SEQ ID NO 8
<211> LENGTH: 75
<212> TYPE: PRT
<213> ORGANISM: Mus musculus

<400> SEQUENCE: 8

Gln Gly Phe Leu Met Phe Lys Gln Gly Arg Cys Leu Cys Ile Gly Pro
1               5                   10                  15

Gly Met Lys Ala Val Lys Met Ala Glu Ile Glu Lys Ala Ser Val Ile
            20                  25                  30

Tyr Pro Ser Asn Gly Cys Asp Lys Val Glu Val Ile Val Thr Met Lys
        35                  40                  45

Ala His Lys Arg Gln Arg Cys Leu Asp Pro Arg Ser Lys Gln Ala Arg
    50                  55                  60

Leu Ile Met Gln Ala Ile Glu Lys Lys Asn Phe
65                  70                  75

<210> SEQ ID NO 9
<211> LENGTH: 75
<212> TYPE: PRT
<213> ORGANISM: Artificial Sequence
<220> FEATURE:
<223> OTHER INFORMATION: Modified human CXCL11 chemokin
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
```

```
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid

<400> SEQUENCE: 9

Gln Gly Phe Xaa Met Phe Lys Xaa Gly Arg Cys Leu Cys Ile Gly Pro
1               5                   10                  15

Gly Xaa Lys Ala Val Lys Xaa Ala Xaa Ile Glu Lys Ala Ser Xaa Xaa
            20                  25                  30

Tyr Pro Ser Asn Xaa Cys Asp Lys Xaa Glu Val Ile Xaa Thr Xaa Lys
            35                  40                  45

Xaa Xaa Lys Xaa Gln Arg Cys Leu Xaa Pro Xaa Ser Lys Gln Ala Arg
        50                  55                  60

Leu Ile Xaa Xaa Xaa Xaa Glu Xaa Lys Asn Phe
65                  70                  75

<210> SEQ ID NO 10
<211> LENGTH: 297
<212> TYPE: PRT
<213> ORGANISM: Bacillus anthracis

<400> SEQUENCE: 10

Met Lys Ala Lys Thr Leu Ser Arg His Leu Arg Glu Gly Val Lys Asn
1               5                   10                  15

Leu Ser Arg Asn Gly Trp Met Thr Phe Ala Ser Val Ser Ala Val Thr
            20                  25                  30

Val Thr Leu Leu Leu Val Gly Val Phe Leu Thr Ala Ile Met Asn Met
            35                  40                  45

Asn His Phe Ala Thr Lys Val Glu Gln Asp Val Glu Ile Arg Val His
        50                  55                  60

Ile Asp Pro Ala Ala Lys Glu Ala Asp Gln Lys Lys Leu Glu Asp Asp
65                  70                  75                  80

Met Ser Lys Ile Ala Lys Val Glu Ser Ile Lys Tyr Ser Ser Lys Glu
                85                  90                  95

Glu Glu Leu Lys Arg Leu Ile Lys Ser Leu Gly Asp Ser Gly Lys Thr
            100                 105                 110

Phe Glu Leu Phe Glu Gln Asp Asn Pro Leu Lys Asn Val Phe Val Val
            115                 120                 125

Lys Ala Lys Glu Pro Thr Asp Thr Ala Thr Ile Ala Lys Lys Ile Glu
        130                 135                 140

Lys Met Gln Phe Val Ser Asn Val Gln Tyr Gly Lys Gly Gln Val Glu
145                 150                 155                 160
```

```
Arg Leu Phe Asp Thr Val Lys Thr Gly Arg Asn Ile Gly Ile Val Leu
                165                 170                 175
Ile Ala Gly Leu Leu Phe Thr Ala Met Phe Leu Ile Ser Asn Thr Ile
            180                 185                 190
Lys Ile Thr Ile Tyr Ala Arg Ser Thr Glu Ile Glu Ile Met Lys Leu
        195                 200                 205
Val Gly Ala Thr Asn Trp Phe Ile Arg Trp Pro Phe Leu Glu Gly
    210                 215                 220
Leu Phe Leu Gly Val Leu Gly Ser Ile Ile Pro Ile Gly Leu Ile Leu
225                 230                 235                 240
Val Thr Tyr Asn Ser Leu Gln Gly Met Phe Asn Glu Lys Leu Gly Gly
                245                 250                 255
Thr Ile Phe Glu Leu Leu Pro Tyr Ser Pro Phe Val Phe Gln Leu Ala
            260                 265                 270
Gly Leu Leu Val Leu Ile Gly Ala Leu Ile Gly Met Trp Gly Ser Val
        275                 280                 285
Met Ser Ile Arg Arg Phe Leu Lys Val
    290                 295
```

<210> SEQ ID NO 11
<211> LENGTH: 894
<212> TYPE: DNA
<213> ORGANISM: Bacillus anthracis

<400> SEQUENCE: 11

```
atgaaggcta agacccttag tcgacatttg cgagaaggtg tgaaaaatct atcccgtaac    60
ggatggatga cgtttgcttc tgttagtgca gtaacagtta cactattact tgtaggtgtc   120
tttttaacag cgattatgaa tatgaaccat tttgcgacga agtagagca agatgttgag    180
attcgtgtac acattgatcc agcagcaaaa gaagctgatc aaaagaaatt agaagatgat   240
atgagtaaga ttgcaaaagt agaatctatt aaatattctt ctaaagaaga gagttaaaa    300
cgtttaatta aaagcttagg cgatagcgga aagacgtttg agttatttga acaagataac   360
ccactgaaaa acgtgttcgt tgtaaaagcg aaagaaccaa cagatacagc aacaattgcg   420
aaaaagattg aaaaaatgca gtttgtaagt aatgttcagt acggaaaagg gcaagttgaa   480
cgattatttg atactgtaaa aactggtcgt aacattggta ttgtgttaat tgctggtctt   540
ttattcacag cgatgttctt aatctctaac acaattaaaa ttacaattta tgctcgtagt   600
acagaaatcg aaattatgaa acttgtaggt gcaacaaact ggtttattcg ttggccgttc   660
ttgttagagg gattattcct aggagtatta ggatcaatta ttccaattgg cttaattctt   720
gttacgtata attcactaca aggtatgttt aacgaaaaac ttggcggaac aattttcgaa   780
cttctaccat atagtccgtt cgtattccaa ttagctggtt tactagtatt aattggggct   840
ttaatcggta tgtggggaag cgtaatgtca attcgtcgtt tcttaaaagt ataa          894
```

<210> SEQ ID NO 12
<211> LENGTH: 88
<212> TYPE: PRT
<213> ORGANISM: Artificial Sequence
<220> FEATURE:
<223> OTHER INFORMATION: Modified human CXCL9 chemokin
<220> FEATURE:
<221> NAME/KEY: MISC_FEATURE
<222> LOCATION: (3)..(3)
<223> OTHER INFORMATION: Xaa at position 3 is any amino acid
<220> FEATURE:
<221> NAME/KEY: MISC_FEATURE
<222> LOCATION: (12)..(12)

```
<223> OTHER INFORMATION: Xaa at position 12 is any amino acid
<220> FEATURE:
<221> NAME/KEY: MISC_FEATURE
<222> LOCATION: (14)..(16)
<223> OTHER INFORMATION: Xaa at positions 14-16 is any amino acid
<220> FEATURE:
<221> NAME/KEY: MISC_FEATURE
<222> LOCATION: (19)..(19)
<223> OTHER INFORMATION: Xaa at positions 19 is Asp, Asn, Glu, Gln, His,
      Arg or Lys
<220> FEATURE:
<221> NAME/KEY: MISC_FEATURE
<222> LOCATION: (22)..(22)
<223> OTHER INFORMATION: Xaa at positions 22 is any amino acid
<220> FEATURE:
<221> NAME/KEY: MISC_FEATURE
<222> LOCATION: (24)..(24)
<223> OTHER INFORMATION: Xaa at position 24 is Valine, Met, Leu, Ile, or
      Cys
<220> FEATURE:
<221> NAME/KEY: MISC_FEATURE
<222> LOCATION: (26)..(27)
<223> OTHER INFORMATION: Xaa at positions 26-27 is any amino acid
<220> FEATURE:
<221> NAME/KEY: MISC_FEATURE
<222> LOCATION: (35)..(36)
<223> OTHER INFORMATION: Xaa at positions 35-36 is Asp, Asn, Glu, Gln,
      His, Arg or Lys
<220> FEATURE:
<221> NAME/KEY: MISC_FEATURE
<222> LOCATION: (41)..(41)
<223> OTHER INFORMATION: Xaa at position 41 is any amino acid
<220> FEATURE:
<221> NAME/KEY: MISC_FEATURE
<222> LOCATION: (42)..(42)
<223> OTHER INFORMATION: Xaa at position 42 is Asp, Asn, Glu, Gln, His,
      Arg or Lys
<220> FEATURE:
<221> NAME/KEY: MISC_FEATURE
<222> LOCATION: (55)..(55)
<223> OTHER INFORMATION: Xaa at position 55 is Ala, Ser, Thr, Pro, Gly
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: MISC_FEATURE
<222> LOCATION: (59)..(59)
<223> OTHER INFORMATION: Xaa at position 59 is any amino acid
<220> FEATURE:
<221> NAME/KEY: MISC_FEATURE
<222> LOCATION: (69)..(69)
<223> OTHER INFORMATION: Xaa at position 69 is any amino acid
<220> FEATURE:
<221> NAME/KEY: MISC_FEATURE
<222> LOCATION: (74)..(74)
<223> OTHER INFORMATION: Xaa at position 74 is Asp, Asn, glu, Gln, His,
      Arg or Lys
<220> FEATURE:
<221> NAME/KEY: MISC_FEATURE
<222> LOCATION: (79)..(79)
<223> OTHER INFORMATION: Xaa at position 79 is Asp, Asn, glu, Gln, His,
      Arg or Lys
<220> FEATURE:
<221> NAME/KEY: MISC_FEATURE
<222> LOCATION: (82)..(82)
<223> OTHER INFORMATION: Xaa at position 82 is Asp, Asn, glu, Gln, His,
      Arg or Lys
<220> FEATURE:
<221> NAME/KEY: MISC_FEATURE
<222> LOCATION: (84)..(84)
<223> OTHER INFORMATION: Xaa at position 84 is Met Leu, Ile, Val or Cys
<220> FEATURE:
<221> NAME/KEY: MISC_FEATURE
<222> LOCATION: (86)..(86)
<223> OTHER INFORMATION: Xaa at position 86 is Asp, Asn, Glu, Gln, His,
      Arg or Lys

<400> SEQUENCE: 12
```

```
Lys Ser Xaa Val Leu Phe Leu Leu Gly Ile Ile Xaa Leu Xaa Xaa Xaa
1               5                   10                  15

Gly Val Xaa Gly Thr Xaa Val Xaa Arg Xaa Xaa Arg Cys Ser Cys Ile
            20              25              30

Ser Thr Xaa Xaa Gly Thr Ile His Xaa Xaa Ser Leu Lys Asp Leu Lys
        35              40              45

Gln Phe Ala Pro Ser Pro Xaa Cys Xaa Lys Xaa Glu Ile Ile Ala Thr
50              55              60

Leu Lys Asn Gly Xaa Gln Thr Cys Leu Xaa Pro Asp Ser Ala Xaa Val
65              70              75              80

Lys Xaa Leu Xaa Lys Xaa Trp Glu
            85
```

```
<210> SEQ ID NO 13
<211> LENGTH: 98
<212> TYPE: PRT
<213> ORGANISM: Artificial Sequence
<220> FEATURE:
<223> OTHER INFORMATION: Modified human CXCL10 chemokin
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa at position 4 is Ala, Ser, thr, Pro or Gly
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa at position 7 is Met, Leu, Ile, Val or Cys
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa at position 22 is Met, Leu, Ile, Val or Cys
<220> FEATURE:
<221> NAME/KEY: MISC_FEATURE
<222> LOCATION: (25)..(25)
<223> OTHER INFORMATION: Xaa at position 25 is Ala, Ser, thr, Pro or Gly
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
```

```
<221> NAME/KEY: MISC_FEATURE
<222> LOCATION: (37)..(37)
<223> OTHER INFORMATION: Xaa at position 37 is Asp, Asn, Glu, Gln, His,
      Arg or Lys
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: MISC_FEATURE
<222> LOCATION: (44)..(44)
<223> OTHER INFORMATION: Xaa at position 44 is  Ala, Ser, thr, Pro or
      Gly
<220> FEATURE:
<221> NAME/KEY: MISC_FEATURE
<222> LOCATION: (45)..(45)
<223> OTHER INFORMATION: Xaa at position 45 is  Met, Leu, Ile, Val or
      Cys
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: MISC_FEATURE
<222> LOCATION: (72)..(72)
<223> OTHER INFORMATION: Xaa at position 72 is Asp, Asn, Glu, Gln, His,
      Arg or Lys
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: MISC_FEATURE
<222> LOCATION: (86)..(86)
<223> OTHER INFORMATION: Xaa at position 86 is Met, Leu, Ile, Val or Cys
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: MISC_FEATURE
<222> LOCATION: (91)..(91)
<223> OTHER INFORMATION: Xaa at position 91 is Asp, Asn, Glu, Gln, His,
      Arg or Lys
<220> FEATURE:
<221> NAME/KEY: MISC_FEATURE
<222> LOCATION: (92)..(92)
<223> OTHER INFORMATION: Xaa at position 92 is Asp, Asn, Glu, Gln, His,
      Arg or Lys
<220> FEATURE:
<221> NAME/KEY: MISC_FEATURE
<222> LOCATION: (97)..(97)
<223> OTHER INFORMATION: Xaa at position 97 is  Ala, Ser, thr, Pro or
      Gly

<400> SEQUENCE: 13

Met Asn Xaa Xaa Ala Xaa Xaa Ile Xaa Cys Leu Ile Xaa Leu Xaa Leu
1               5                   10                  15

Ser Gly Xaa Gln Gly Xaa Pro Leu Xaa Arg Thr Val Arg Cys Xaa Cys
            20                  25                  30

Ile Xaa Ile Xaa Xaa Xaa Pro Val Xaa Xaa Arg Xaa Xaa Xaa Lys Leu
        35                  40                  45

Glu Ile Ile Pro Ala Ser Xaa Xaa Cys Pro Arg Val Glu Ile Ile Ala
```

```
                50                  55                  60
Thr Met Lys Lys Xaa Xaa Glu Xaa Arg Cys Leu Asn Pro Glu Ser Lys
 65                  70                  75                  80

Xaa Ile Lys Asn Leu Xaa Lys Ala Xaa Ser Xaa Xaa Arg Ser Lys Arg
                 85                  90                  95

Xaa Pro

<210> SEQ ID NO 14
<211> LENGTH: 75
<212> TYPE: PRT
<213> ORGANISM: Artificial Sequence
<220> FEATURE:
<223> OTHER INFORMATION: Modified human CXCL11 chemokin
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa at position 8 is Asp, Asn, Glu, Gln, His,
      Arg, or Lys
<220> FEATURE:
<221> NAME/KEY: MISC_FEATURE
<222> LOCATION: (18)..(18)
<223> OTHER INFORMATION: Xaa at position 18 is Met, Leu, Ile, Val, or
      Cys
<220> FEATURE:
<221> NAME/KEY: MISC_FEATURE
<222> LOCATION: (23)..(23)
<223> OTHER INFORMATION: Xaa at position 23 is Met, Leu, Ile, Val, or
      Cys
<220> FEATURE:
<221> NAME/KEY: MISC_FEATURE
<222> LOCATION: (25)..(25)
<223> OTHER INFORMATION: Xaa at position 25 is Asp, Asn, Glu, Gln, His,
      Arg, or Lys
<220> FEATURE:
<221> NAME/KEY: MISC_FEATURE
<222> LOCATION: (31)..(32)
<223> OTHER INFORMATION: Xaa at positions 31-32 are independently Met,
      Leu, Ile, Val, or Cys
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: MISC_FEATURE
<222> LOCATION: (41)..(41)
<223> OTHER INFORMATION: Xaa at position 41 is Met, Leu, Ile, Val, or
      Cys
<220> FEATURE:
<221> NAME/KEY: MISC_FEATURE
<222> LOCATION: (45)..(45)
<223> OTHER INFORMATION: Xaa at position 45 is Met, Leu, Ile, Val, or
      Cys
<220> FEATURE:
<221> NAME/KEY: MISC_FEATURE
<222> LOCATION: (47)..(47)
<223> OTHER INFORMATION: Xaa at position 47 is Met, Leu, Ile, Val, or
      Cys
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: MISC_FEATURE
<222> LOCATION: (50)..(50)
<223> OTHER INFORMATION: Xaa at position 50 is Asp, Asn, Glu, Gln, His,
      Arg, or Lys
<220> FEATURE:
<221> NAME/KEY: misc_feature
<222> LOCATION: (52)..(52)
<223> OTHER INFORMATION: Xaa can be any naturally occurring amino acid
<220> FEATURE:
```

```
<221> NAME/KEY: MISC_FEATURE
<222> LOCATION: (57)..(57)
<223> OTHER INFORMATION: Xaa at position 57 is Asp, Asn, Glu, Gln, His,
      Arg, or Lys
<220> FEATURE:
<221> NAME/KEY: MISC_FEATURE
<222> LOCATION: (59)..(59)
<223> OTHER INFORMATION: Xaa at position 59 is Asp, Asn, Glu, Gln, His,
      Arg, or Lys
<220> FEATURE:
<221> NAME/KEY: MISC_FEATURE
<222> LOCATION: (67)..(67)
<223> OTHER INFORMATION: Xaa at position 67 is Met, Leu, Ile, Val, or
      Cys
<220> FEATURE:
<221> NAME/KEY: MISC_FEATURE
<222> LOCATION: (68)..(68)
<223> OTHER INFORMATION: Xaa at position 68 is Asp, Asn, Glu, Gln, His,
      Arg, or Lys
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: MISC_FEATURE
<222> LOCATION: (70)..(70)
<223> OTHER INFORMATION: Xaa at position 70 is Met, Leu, Ile, Val, or
      Cys
<220> FEATURE:
<221> NAME/KEY: MISC_FEATURE
<222> LOCATION: (72)..(72)
<223> OTHER INFORMATION: Xaa at position 72 is Asp, Asn, Glu, Gln, His,
      Arg, or Lys

<400> SEQUENCE: 14

Gln Gly Phe Xaa Met Phe Lys Xaa Gly Arg Cys Leu Cys Ile Gly Pro
1               5                   10                  15

Gly Xaa Lys Ala Val Lys Xaa Ala Xaa Ile Glu Lys Ala Ser Xaa Xaa
            20                  25                  30

Tyr Pro Ser Asn Xaa Cys Asp Lys Xaa Glu Val Ile Xaa Thr Xaa Lys
            35                  40                  45

Xaa Xaa Lys Xaa Gln Arg Cys Leu Xaa Pro Xaa Ser Lys Gln Ala Arg
    50                  55                  60

Leu Ile Xaa Xaa Xaa Xaa Glu Xaa Lys Asn Phe
65                  70                  75

<210> SEQ ID NO 15
<211> LENGTH: 88
<212> TYPE: PRT
<213> ORGANISM: Artificial Sequence
<220> FEATURE:
<223> OTHER INFORMATION: Modified human CXCL9 chemokin
<220> FEATURE:
<221> NAME/KEY: MISC_FEATURE
<222> LOCATION: (19)..(19)
<223> OTHER INFORMATION: Xaa at positions 19 is Asp, Asn, Glu, Gln, His,
      Arg or Lys
<220> FEATURE:
<221> NAME/KEY: MISC_FEATURE
<222> LOCATION: (24)..(24)
<223> OTHER INFORMATION: Xaa at position 24 is Valine, Met, Leu, Ile, or
      Cys
<220> FEATURE:
<221> NAME/KEY: MISC_FEATURE
<222> LOCATION: (35)..(36)
<223> OTHER INFORMATION: Xaa at positions 35-36 is Asp, Asn, Glu, Gln,
      His, Arg or Lys
<220> FEATURE:
<221> NAME/KEY: MISC_FEATURE
<222> LOCATION: (42)..(42)
<223> OTHER INFORMATION: Xaa at position 42 is Asp, Asn, Glu, Gln, His,
      Arg or Lys
<220> FEATURE:
```

-continued

```
<221> NAME/KEY: MISC_FEATURE
<222> LOCATION: (55)..(55)
<223> OTHER INFORMATION: Xaa at position 55 is Ala, Ser, Thr, Pro, or
      Gly
<220> FEATURE:
<221> NAME/KEY: MISC_FEATURE
<222> LOCATION: (74)..(74)
<223> OTHER INFORMATION: Xaa at position 74 is Asp, Asn, glu, Gln, His,
      Arg or Lys
<220> FEATURE:
<221> NAME/KEY: MISC_FEATURE
<222> LOCATION: (79)..(79)
<223> OTHER INFORMATION: Xaa at position 79 is Asp, Asn, glu, Gln, His,
      Arg or Lys
<220> FEATURE:
<221> NAME/KEY: MISC_FEATURE
<222> LOCATION: (82)..(82)
<223> OTHER INFORMATION: Xaa at position 82 is Asp, Asn, Glu, Gln, His,
      Arg or Lys
<220> FEATURE:
<221> NAME/KEY: MISC_FEATURE
<222> LOCATION: (84)..(84)
<223> OTHER INFORMATION: Xaa at position 84 is Met Leu, Ile, Val or Cys
<220> FEATURE:
<221> NAME/KEY: MISC_FEATURE
<222> LOCATION: (86)..(86)
<223> OTHER INFORMATION: Xaa at position 86 is Asp, Asn, Glu, Gln, His,
      Arg or Lys

<400> SEQUENCE: 15

Lys Ser Gly Val Leu Phe Leu Leu Gly Ile Ile Leu Leu Val Leu Ile
1               5                   10                  15

Gly Val Xaa Gly Thr Pro Val Xaa Arg Lys Gly Arg Cys Ser Cys Ile
            20                  25                  30

Ser Thr Xaa Xaa Gly Thr Ile His Leu Xaa Ser Leu Lys Asp Leu Lys
        35                  40                  45

Gln Phe Ala Pro Ser Pro Xaa Cys Glu Lys Ile Glu Ile Ile Ala Thr
    50                  55                  60

Leu Lys Asn Gly Val Gln Thr Cys Leu Xaa Pro Asp Ser Ala Xaa Val
65                  70                  75                  80

Lys Xaa Leu Xaa Lys Xaa Trp Glu
                85

<210> SEQ ID NO 16
<211> LENGTH: 98
<212> TYPE: PRT
<213> ORGANISM: Artificial Sequence
<220> FEATURE:
<223> OTHER INFORMATION: Modified human CXCL10 chemokin
<220> FEATURE:
<221> NAME/KEY: MISC_FEATURE
<222> LOCATION: (4)..(4)
<223> OTHER INFORMATION: Xaa at position 4 is Ala, Ser, thr, Pro or Gly
<220> FEATURE:
<221> NAME/KEY: MISC_FEATURE
<222> LOCATION: (7)..(7)
<223> OTHER INFORMATION: Xaa at position 7 is Met, Leu, Ile, Val or Cys
<220> FEATURE:
<221> NAME/KEY: MISC_FEATURE
<222> LOCATION: (22)..(22)
<223> OTHER INFORMATION: Xaa at position 22 is Met, Leu, Ile, Val or Cys
<220> FEATURE:
<221> NAME/KEY: MISC_FEATURE
<222> LOCATION: (25)..(25)
<223> OTHER INFORMATION: Xaa at position 25 is Ala, Ser, thr, Pro or Gly
<220> FEATURE:
<221> NAME/KEY: MISC_FEATURE
<222> LOCATION: (37)..(37)
<223> OTHER INFORMATION: Xaa at position 37 is Asp, Asn, Glu, Gln, His,
      Arg or Lys
<220> FEATURE:
<221> NAME/KEY: MISC_FEATURE
```

```
<222> LOCATION: (44)..(44)
<223> OTHER INFORMATION: Xaa at position 44 is  Ala, Ser, thr, Pro or
      Gly
<220> FEATURE:
<221> NAME/KEY: MISC_FEATURE
<222> LOCATION: (45)..(45)
<223> OTHER INFORMATION: Xaa at position 45 is  Met, Leu, Ile, Val or
      Cys
<220> FEATURE:
<221> NAME/KEY: MISC_FEATURE
<222> LOCATION: (72)..(72)
<223> OTHER INFORMATION: Xaa at position 72 is Asp, Asn, Glu, Gln, His,
      Arg or Lys
<220> FEATURE:
<221> NAME/KEY: MISC_FEATURE
<222> LOCATION: (86)..(86)
<223> OTHER INFORMATION: Xaa at position 86 is Met, Leu, Ile, Val or Cys
<220> FEATURE:
<221> NAME/KEY: MISC_FEATURE
<222> LOCATION: (91)..(91)
<223> OTHER INFORMATION: Xaa at position 91 is Asp, Asn, Glu, Gln, His,
      Arg or Lys
<220> FEATURE:
<221> NAME/KEY: MISC_FEATURE
<222> LOCATION: (92)..(92)
<223> OTHER INFORMATION: Xaa at position 92 is Asp, Asn, Glu, Gln, His,
      Arg or Lys
<220> FEATURE:
<221> NAME/KEY: MISC_FEATURE
<222> LOCATION: (97)..(97)
<223> OTHER INFORMATION: Xaa at position 97 is  Ala, Ser, thr, Pro or
      Gly

<400> SEQUENCE: 16

Met Asn Gln Xaa Ala Ile Xaa Ile Cys Cys Leu Ile Phe Leu Thr Leu
1               5                   10                  15

Ser Gly Ile Gln Gly Xaa Pro Leu Xaa Arg Thr Val Arg Cys Thr Cys
            20                  25                  30

Ile Ser Ile Ser Xaa Gln Pro Val Asn Pro Arg Xaa Xaa Glu Lys Leu
        35                  40                  45

Glu Ile Ile Pro Ala Ser Gln Phe Cys Pro Arg Val Glu Ile Ile Ala
50                  55                  60

Thr Met Lys Lys Lys Gly Glu Xaa Arg Cys Leu Asn Pro Glu Ser Lys
65                  70                  75                  80

Ala Ile Lys Asn Leu Xaa Lys Ala Val Ser Xaa Xaa Arg Ser Lys Arg
                85                  90                  95

Xaa Pro

<210> SEQ ID NO 17
<211> LENGTH: 75
<212> TYPE: PRT
<213> ORGANISM: Artificial Sequence
<220> FEATURE:
<223> OTHER INFORMATION: Modified human CXCL11 chemokin
<220> FEATURE:
<221> NAME/KEY: MISC_FEATURE
<222> LOCATION: (8)..(8)
<223> OTHER INFORMATION: Xaa at position 8 is Asp, Asn, Glu, Gln, His,
      Arg, or Lys
<220> FEATURE:
<221> NAME/KEY: MISC_FEATURE
<222> LOCATION: (18)..(18)
<223> OTHER INFORMATION: Xaa at position 18 is Met, Leu, Ile, Val, or
      Cys
<220> FEATURE:
<221> NAME/KEY: MISC_FEATURE
<222> LOCATION: (23)..(23)
<223> OTHER INFORMATION: Xaa at position 23 is Met, Leu, Ile, Val, or
      Cys
<220> FEATURE:
<221> NAME/KEY: MISC_FEATURE
```

```
<222> LOCATION: (25)..(25)
<223> OTHER INFORMATION: Xaa at position 25 is Asp, Asn, Glu, Gln, His,
      Arg, or Lys
<220> FEATURE:
<221> NAME/KEY: MISC_FEATURE
<222> LOCATION: (31)..(32)
<223> OTHER INFORMATION: Xaa at positions 31-32 are independently Met,
      Leu, Ile, Val, or Cys
<220> FEATURE:
<221> NAME/KEY: MISC_FEATURE
<222> LOCATION: (41)..(41)
<223> OTHER INFORMATION: Xaa at position 41 is Met, Leu, Ile, Val, or
      Cys
<220> FEATURE:
<221> NAME/KEY: MISC_FEATURE
<222> LOCATION: (45)..(45)
<223> OTHER INFORMATION: Xaa at position 45 is Met, Leu, Ile, Val, or
      Cys
<220> FEATURE:
<221> NAME/KEY: MISC_FEATURE
<222> LOCATION: (47)..(47)
<223> OTHER INFORMATION: Xaa at position 47 is Met, Leu, Ile, Val, or
      Cys
<220> FEATURE:
<221> NAME/KEY: MISC_FEATURE
<222> LOCATION: (50)..(50)
<223> OTHER INFORMATION: Xaa at position 50 is Asp, Asn, Glu, Gln, His,
      Arg, or Lys
<220> FEATURE:
<221> NAME/KEY: MISC_FEATURE
<222> LOCATION: (57)..(57)
<223> OTHER INFORMATION: Xaa at position 57 is Asp, Asn, Glu, Gln, His,
      Arg, or Lys
<220> FEATURE:
<221> NAME/KEY: MISC_FEATURE
<222> LOCATION: (59)..(59)
<223> OTHER INFORMATION: Xaa at position 59 is Asp, Asn, Glu, Gln, His,
      Arg, or Lys
<220> FEATURE:
<221> NAME/KEY: MISC_FEATURE
<222> LOCATION: (67)..(67)
<223> OTHER INFORMATION: Xaa at position 67 is Met, Leu, Ile, Val, or
      Cys
<220> FEATURE:
<221> NAME/KEY: MISC_FEATURE
<222> LOCATION: (68)..(68)
<223> OTHER INFORMATION: Xaa at position 68 is Asp, Asn, Glu, Gln, His,
      Arg, or Lys
<220> FEATURE:
<221> NAME/KEY: MISC_FEATURE
<222> LOCATION: (70)..(70)
<223> OTHER INFORMATION: Xaa at position 70 is Met, Leu, Ile, Val, or
      Cys
<220> FEATURE:
<221> NAME/KEY: MISC_FEATURE
<222> LOCATION: (72)..(72)
<223> OTHER INFORMATION: Xaa at position 72 is Asp, Asn, Glu, Gln, His,
      Arg, or Lys

<400> SEQUENCE: 17

Gln Gly Phe Pro Met Phe Lys Xaa Gly Arg Cys Leu Cys Ile Gly Pro
1               5                   10                  15

Gly Xaa Lys Ala Val Lys Xaa Ala Xaa Ile Glu Lys Ala Ser Xaa Xaa
                20                  25                  30

Tyr Pro Ser Asn Asn Cys Asp Lys Xaa Glu Val Ile Xaa Thr Xaa Lys
            35                  40                  45

Glu Xaa Lys Gly Gln Arg Cys Leu Xaa Pro Xaa Ser Lys Gln Ala Arg
    50                  55                  60

Leu Ile Xaa Xaa Lys Xaa Glu Xaa Lys Asn Phe
65                  70                  75

<210> SEQ ID NO 18
<211> LENGTH: 27
```

```
<212> TYPE: PRT
<213> ORGANISM: Bacillus anthracis

<400> SEQUENCE: 18

Lys Val Glu Gln Asp Val Glu Ile Arg Val His Ile Asp Pro Ala Ala
1               5                   10                  15

Lys Glu Ala Asp Gln Lys Lys Leu Glu Asp Asp
            20                  25
```